US011576868B2

(12) United States Patent
Zatechka et al.

(10) Patent No.: US 11,576,868 B2
(45) Date of Patent: Feb. 14, 2023

(54) METHOD FOR REDUCING ZOONOTIC INFECTIOUS DISEASES

(71) Applicant: US Biologic, Inc., Memphis, TN (US)

(72) Inventors: Douglas Steven Zatechka, Cordova, TN (US); Mason Kauffman, Memphis, TN (US); Chris Przybyszewski, Southaven, MS (US)

(73) Assignee: US Biologic, Inc., Memphis, TN (US)

( * ) Notice: Subject to any disclaimer, the term of this patent is extended or adjusted under 35 U.S.C. 154(b) by 7 days.

(21) Appl. No.: 16/848,841

(22) Filed: Apr. 15, 2020

(65) Prior Publication Data

US 2021/0069116 A1 Mar. 11, 2021

Related U.S. Application Data

(60) Division of application No. 15/386,695, filed on Dec. 21, 2016, now Pat. No. 10,653,630, which is a continuation-in-part of application No. PCT/US2015/037925, filed on Jun. 26, 2015.

(60) Provisional application No. 62/017,699, filed on Jun. 26, 2014.

(51) Int. Cl.
| | | |
|---|---|---|
| *A61K 9/28* | (2006.01) | |
| *A61K 39/09* | (2006.01) | |
| *A61K 39/00* | (2006.01) | |
| *A61K 9/50* | (2006.01) | |
| *A23K 10/18* | (2016.01) | |
| *A23K 40/20* | (2016.01) | |
| *A61K 39/02* | (2006.01) | |
| *A23K 40/30* | (2016.01) | |
| *A61K 9/00* | (2006.01) | |
| *A23K 10/16* | (2016.01) | |
| *A61K 39/108* | (2006.01) | |

(52) U.S. Cl.
CPC .............. *A61K 9/282* (2013.01); *A23K 10/16* (2016.05); *A23K 10/18* (2016.05); *A23K 40/20* (2016.05); *A23K 40/30* (2016.05); *A61K 9/0056* (2013.01); *A61K 39/00* (2013.01); *A61K 39/0225* (2013.01); *A61K 39/0258* (2013.01); *A61K 39/09* (2013.01); *A61K 9/5015* (2013.01); *A61K 9/5078* (2013.01); *A61K 2039/523* (2013.01); *A61K 2039/542* (2013.01); *A61K 2039/552* (2013.01)

(58) Field of Classification Search
None
See application file for complete search history.

*Primary Examiner* — Oluwatosin A Ogunbiyi
(74) *Attorney, Agent, or Firm* — William S. Parks; Susan Fentress

(57) ABSTRACT

The presently disclosed subject matter relates to a composition and method of using the composition for oral delivery of a bioactive agent to a subject. More particularly, the presently disclosed subject matter relates to a composition comprising an effective amount of at least one bioactive agent layered over a substrate and a method of reducing zoonotic infectious disease by administering the composition to a subject. The presently disclosed subject matter further relates to a method of preparing the composition.

13 Claims, 12 Drawing Sheets

Specification includes a Sequence Listing.

FIGURE 3

SEQ ID NO: 3

| Score | Expect | Identities | Gaps | Strand |
|---|---|---|---|---|
| 1519 bits(822) | 0.0 | 822/822(100%) | 0/822(0%) | Plus/Plus |

```
Query    1    ATGAAAAAATATTTATTGGGAATAGGTCTAATATTAGCCTTAATAGCATGTAAGCAAAAT    60
              ||||||||||||||||||||||||||||||||||||||||||||||||||||||||||||
Sbjct    50   ATGAAAAAATATTTATTGGGAATAGGTCTAATATTAGCCTTAATAGCATGTAAGCAAAAT    109

Query    61   GTTAGCAGCCTTGACGAGAAAAACAGCGTTTCAGTAGATTTGCCTGGTGAAATGAAAGTT   120
              ||||||||||||||||||||||||||||||||||||||||||||||||||||||||||||
Sbjct    110  GTTAGCAGCCTTGACGAGAAAAACAGCGTTTCAGTAGATTTGCCTGGTGAAATGAAAGTT   169

Query    121  CTTGTAAGCAAAGaaaaaaaCAAAGACGGCAAGTACGATCTAATTGCAACAGTAGACAAG   180
              ||||||||||||||       |||||||||||||||||||||||||||||||||||||||
Sbjct    170  CTTGTAAGCAAAGAAAAAAACAAAGACGGCAAGTACGATCTAATTGCAACAGTAGACAAG   229

Query    181  CTTGAGCTTAAAGGAACTTCTGATAAAAACAATGGATCTGGAGTACTTGAAGGCGTAAAA   240
              ||||||||||||||||||||||||||||||||||||||||||||||||||||||||||||
Sbjct    230  CTTGAGCTTAAAGGAACTTCTGATAAAAACAATGGATCTGGAGTACTTGAAGGCGTAAAA   289

Query    241  GCTGACAAAAGTAAAGTAAAATTAACAATTTCTGACGATCTAGGTCAAACCACACTTGAA   300
              ||||||||||||||||||||||||||||||||||||||||||||||||||||||||||||
Sbjct    290  GCTGACAAAAGTAAAGTAAAATTAACAATTTCTGACGATCTAGGTCAAACCACACTTGAA   349

Query    301  GTTTTCAAAGAAGATGGCAAAACACTAGTATCaaaaaaaGTAACTTCCAAAGACAAGTCA   360
              |||||||||||||||||||||||||||||||       ||||||||||||||||||||||
Sbjct    350  GTTTTCAAAGAAGATGGCAAAACACTAGTATCAAAAAAAGTAACTTCCAAAGACAAGTCA   409

Query    361  TCAACAGAAGAAAAATCAATGAAAAAGGTGAAGTATCTGAAAAAATAATAACAAGAGCA   420
              ||||||||||||||||||||||||||||||||||||||||||||||||||||||||||||
Sbjct    410  TCAACAGAAGAAAAATCAATGAAAAAGGTGAAGTATCTGAAAAAATAATAACAAGAGCA   469

Query    421  GACGGAACCAGACTTGAATACACAGGAATTAAAAGCGATGGATCTGGAAAAGCTAAAGAG   480
              ||||||||||||||||||||||||||||||||||||||||||||||||||||||||||||
Sbjct    470  GACGGAACCAGACTTGAATACACAGGAATTAAAAGCGATGGATCTGGAAAAGCTAAAGAG   529

Query    481  GTTTTAAAAGGCTATGTTCTTGAAGGAACTCTAACTGCTGAAAAAACAACATTGGTGGTT   540
              ||||||||||||||||||||||||||||||||||||||||||||||||||||||||||||
Sbjct    530  GTTTTAAAAGGCTATGTTCTTGAAGGAACTCTAACTGCTGAAAAAACAACATTGGTGGTT   589

Query    541  AAAGAAGGAACTGTTACTTTAAGCAAAAATATTTCAAAATCTGGGGAAGTTTCAGTTGAA   600
              ||||||||||||||||||||||||||||||||||||||||||||||||||||||||||||
Sbjct    590  AAAGAAGGAACTGTTACTTTAAGCAAAAATATTTCAAAATCTGGGGAAGTTTCAGTTGAA   649

Query    601  CTTAATGACACTGACAGTAGTGCTGCTACTaaaaaaaCTGCAGCTTGGAATTCAGGCACT   660
              ||||||||||||||||||||||||||||||       |||||||||||||||||||||||
Sbjct    650  CTTAATGACACTGACAGTAGTGCTGCTACTAAAAAAACTGCAGCTTGGAATTCAGGCACT   709

Query    661  TCAACTTTAACAATTACTGTAACAGTaaaaaaaCTAAAGACCTTGTGTTTACAAAAGAA   720
              |||||||||||||||||||||||||       ||||||||||||||||||||||||||||
Sbjct    710  TCAACTTTAACAATTACTGTAACAGTAAAAAAACTAAAGACCTTGTGTTTACAAAAGAA   769

Query    721  AACACAATTACAGTACAACAATACGACTCAAATGGCACCAAATTAGAGGGGTCAGCAGTT   780
              ||||||||||||||||||||||||||||||||||||||||||||||||||||||||||||
Sbjct    770  AACACAATTACAGTACAACAATACGACTCAAATGGCACCAAATTAGAGGGGTCAGCAGTT   829

Query    781  GAAATTACAAAACTTGATGAAATTAAAAACGCTTTAAAATAA   822
              ||||||||||||||||||||||||||||||||||||||||||
Sbjct    830  GAAATTACAAAACTTGATGAAATTAAAAACGCTTTAAAATAA   871
```

FIGURE 4

SEQ ID NO: 3

| Score | Expect | Identities | Gaps | Strand |
|---|---|---|---|---|
| 1515 bits(820) | 0.0 | 821/822(99%) | 0/822(0%) | Plus/Minus |

```
Query  1    ATGAAAAATATTAATTGGAATAGGTCTAATATTAGCCTTAATAGCATGTAAGCAAAAT    60
            ||||||||||||||||||||||||| |||||||||||||||||||||||||||||||||
Sbjct  862  ATGAAAAATATTAATTGGAATAGGTNTAATATTAGCCTTAATAGCATGTAAGCAAAAT    803

Query  61   GTTAGCAGCCTTGACGAGAAAAACAGCGTTTCAGTAGATTTGCCTGGTGAAATGAAAGTT  120
            ||||||||||||||||||||||||||||||||||||||||||||||||||||||||||||
Sbjct  802  GTTAGCAGCCTTGACGAGAAAAACAGCGTTTCAGTAGATTTGCCTGGTGAAATGAAAGTT  743

Query  121  CTTGTAAGCAAGaaaaaaaCAAAGACGGCAAGTACGATCTAATTGCAACAGTAGACAAG  180
            ||||||||||||       |||||||||||||||||||||||||||||||||||||||
Sbjct  742  CTTGTAAGCAAGAAAAAAACAAAGACGGCAAGTACGATCTAATTGCAACAGTAGACAAG  683

Query  181  CTTGAGCTTAAAGGAACTTCTGATAAAAACAATGGATCTGGAGTACTTGAAGGCGTAAAA  240
            ||||||||||||||||||||||||||||||||||||||||||||||||||||||||||||
Sbjct  682  CTTGAGCTTAAAGGAACTTCTGATAAAAACAATGGATCTGGAGTACTTGAAGGCGTAAAA  623

Query  241  GCTGACAAAAGTAAAGTAAAATTAACAATTTCTGACGATCTAGGTCAAACCACACTTGAA  300
            ||||||||||||||||||||||||||||||||||||||||||||||||||||||||||||
Sbjct  622  GCTGACAAAAGTAAAGTAAAATTAACAATTTCTGACGATCTAGGTCAAACCACACTTGAA  563

Query  301  GTTTTCAAAGAAGATGGCAAAACACTAGTATCaaaaaaaGTAACTTCCAAAGACAAGTCA  360
            |||||||||||||||||||||||||||||||       ||||||||||||||||||||
Sbjct  562  GTTTTCAAAGAAGATGGCAAAACACTAGTATCAAAAAAAGTAACTTCCAAAGACAAGTCA  503

Query  361  TCAACGAAGAAAAATTCAATGAAAAAGGTGAAGTATCTGAAAAAATAATAACAAGAGCA  420
            ||||||||||||||||||||||||||||||||||||||||||||||||||||||||||||
Sbjct  502  TCAACGAAGAAAAATTCAATGAAAAAGGTGAAGTATCTGAAAAAATAATAACAAGAGCA  443

Query  421  GACGGAACCAGACTTGAATACACAGGAATTAAAGCGATGGATCTGGAAAAGCTAAAGAG  480
            ||||||||||||||||||||||||||||||||||||||||||||||||||||||||||||
Sbjct  442  GACGGAACCAGACTTGAATACACAGGAATTAAAGCGATGGATCTGGAAAAGCTAAAGAG  383

Query  481  GTTTTAAAGGCTATGTTCTTGAAGGAACTCTAACTGCTGAAAAAACAACATTGGTGGTT  540
            ||||||||||||||||||||||||||||||||||||||||||||||||||||||||||||
Sbjct  382  GTTTTAAAGGCTATGTTCTTGAAGGAACTCTAACTGCTGAAAAAACAACATTGGTGGTT  323

Query  541  AAAGAAGGAACTGTTACTTTAAGCAAAAATATTTCAAAATCTGGGGAAGTTTCAGTTGAA  600
            ||||||||||||||||||||||||||||||||||||||||||||||||||||||||||||
Sbjct  322  AAAGAAGGAACTGTTACTTTAAGCAAAAATATTTCAAAATCTGGGGAAGTTTCAGTTGAA  263

Query  601  CTTAATGACACTGACAGTAGTGCTGCTACTaaaaaaaCTGCAGCTTGGAATTCAGGCACT  660
            |||||||||||||||||||||||||||||       |||||||||||||||||||||||
Sbjct  262  CTTAATGACACTGACAGTAGTGCTGCTACTAAAAAAACTGCAGCTTGGAATTCAGGCACT  203

Query  661  TCAACTTTAACAATTACTGTAAACAGTaaaaaaaCTAAAGACCTTGTGTTTACAAAAGAA  720
            |||||||||||||||||||||||||||       ||||||||||||||||||||||||
Sbjct  202  TCAACTTTAACAATTACTGTAAACAGTAAAAAAACTAAAGACCTTGTGTTTACAAAAGAA  143

Query  721  AACACAATTACAGTACAACAATACGACTCAAATGGCACCAAATTAGAGGGTCAGCAGTT  780
            ||||||||||||||||||||||||||||||||||||||||||||||||||||||||||||
Sbjct  142  AACACAATTACAGTACAACAATACGACTCAAATGGCACCAAATTAGAGGGTCAGCAGTT  83

Query  781  GAAATTACAAAACTTGATGAAATTAAAAACGCTTTAAAATAA  822
            ||||||||||||||||||||||||||||||||||||||||||
Sbjct  82   GAAATTACAAAACTTGATGAAATTAAAAACGCTTTAAAATAA  41
```

FIGURE 7

Sprayed Stabilized Bacteria

Sprayed Cross-linker / Glaze/Shellac- flavoring Binding Solution

Substrates → Bacterial-coated Substrates → Finished Substrates

METHOD FOR REDUCING ZOONOTIC INFECTIOUS DISEASES

RELATED APPLICATIONS

This application is a divisional of U.S. patent application Ser. No. 15/386,995, filed on Dec. 21, 2016, now U.S. patent Ser. No. 10/653,630, which is a continuation-in-part of PCT application No. PCT/US2015/037925, filed Jun. 26, 2015, which claims priority to U.S. Provisional Patent Application No. 62/017,699, filed Jun. 26, 2014, and the entire disclosures of which are hereby incorporated by reference in their entireties.

TECHNICAL FIELD

The presently disclosed subject matter relates to a composition and method of using the composition for oral delivery of a bioactive agent to a subject. More particularly, the presently disclosed subject matter relates to a composition comprising a substrate and an effective amount of at least one bioactive agent layered over the substrate and a method of reducing zoonotic infectious disease. The presently disclosed subject matter further relates to a method of preparing the composition.

BACKGROUND OF THE INVENTION

Controlling zoonotic infectious diseases and antimicrobial resistance contributes to the reduction of disease transmissibility. Current strategies to control zoonotic infectious diseases include the deployment of pesticides as a means to eliminate the vector from the enzootic cycle. However, the use of pesticides presents with toxic off-target effects upon the disease reservoir host subject and environment. The use of prophylactic and therapeutic antibiotics, concomitantly, has inadvertently led to the evolution of antimicrobial-resistant strains of infectious agents being introduced and subsequently maintained in the zoonotic cycle. Further, while targeting susceptible disease reservoir hosts with prophylactic or therapeutic agent campaigns often employ parenteral administration, such administrative methods pose cost and logistics challenges. Orally delivered prophylactic or therapeutic agents are manufactured cost effectively, offer a significant ease of use as reservoir targeted vaccines (RTVs) with broad and wide-spread applicability, and cause few side effects.

SUMMARY OF THE INVENTION

This Summary describes several embodiments of the presently disclosed subject matter, and, in many cases, lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter relates to a composition and method of using the composition for oral delivery of a bioactive agent to a subject. More particularly, the presently disclosed subject matter relates to a composition comprising a substrate and an effective amount of at least one bioactive agent layered over the substrate and a method of reducing zoonotic infectious disease. In some embodiments, the presently disclosed subject matter provides a method to reduce antimicrobial resistance by administering the composition to a subject.

In some embodiments of the presently disclosed subject matter, a composition is provided. The composition includes a substrate, an effective amount at least one bioactive agent, and a cross-linking agent. In some embodiments, the at least one bioactive agent is layered over the substrate. In some embodiments, the bioactive agent is osmotically preconditioned in an osmotic preconditioner. In some embodiments, the at least one bioactive agent is stabilized in a stabilizer matrix for substrate application. In some embodiments, the at least one bioactive agent is stabilized in a stabilizer matrix under conditions facilitating anhydrobiosis. In some embodiments, the cross-linking agent is sequentially incorporated with the stabilizer matrix to polymerize the stabilizer matrix for stabilization of the at least one bioactive antigenic agent under conditions facilitating anhydrobiosis. In some embodiments, the substrate comprises a medium to deliver orally consumed vaccines or other therapeutics. In some embodiments, the substrate is a bait. In some embodiments, the at least one bioactive antigenic agent is stabilized under conditions facilitating anhydrobiosis through air drying. In some embodiments, the composition comprises a coating or shell on the exterior surface of the composition. In some embodiments, the coating comprises the bioactive agent and the cross-linking agent. In some embodiments, the coating on the exterior surface comprises an enteric coating. In some embodiments, the coating comprises shellac coating. In some embodiments, the composition further comprises a coating with a confectionary glaze layer on the exterior surface for moisture barrier or flavored attractant.

In some embodiments, the composition comprises a bioactive agent prepared by the steps of (1) passaging and culturing the at least one bioactive agent under specific induction conditions, (2) osmotically preconditioning the at least one bioactive agent, and (3) stabilizing at least one bioactive agent in a liquid polymeric stabilizer carrier for application. In some embodiments, the steps further comprise applying the stabilized at least one bioactive agent as a coating onto a surface of a substrate. In some embodiments, the steps further comprise subsequently cross-linking the stabilized at least one bioactive agent by applying a cross-linking agent to the substrate. In some embodiments, the steps further comprise drying under forced air at ambient temperatures in a range of temperatures. In some embodiments, the temperature is between about 20° C. to about 35° C.

In some embodiments, the composition comprises a bioactive agent prepared by the steps of (1) passaging and culturing the at least one bioactive agent under specific induction conditions, (2) osmotically preconditioning the at least one bioactive agent, (3) stabilizing at least one bioactive agent in a liquid polymeric stabilizer carrier for application. In some embodiments, the steps further comprise electrospraying the stabilized at least one bioactive agent as an atomized formulation into a cross-linking agent bath. In some embodiments, the steps further comprise collecting the composition as a microencapsulated bead. In some embodiments, the steps further comprise drying by lyophilizing or air drying under forced air at ambient temperatures in a range of temperatures between 20° C. to about 35° C. for application as a hydrocolloid. In some embodiments, the hydrocolloid is water-based.

In some embodiments, the substrate has a mean diameter of from about 100 µm to about 2 cm. The diameter is about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, about 1 cm, about 11 mm, about 12 mm, about 13 mm, about 14 mm, about 15 mm, about 16 mm, about 17 mm, about 18 mm, about 19 mm, about 2 cm. In some embodiments, the microencapsulated bead has a mean diameter of from about 5 µm to about 100 µm.

In some embodiments, the osmotic preconditioner includes, but is not limited to, a sugar solution of a saline solvent base. In some embodiments, the sugar solution includes non-limiting examples of sucrose or trehalose. In some embodiments, the saline solvent base includes non-limiting examples of phosphate-buffered saline. In some embodiments, the stabilizer or stabilizer matrix comprises a polymeric matrix comprising a hydrocolloid polymer. In some embodiments, a non-limiting example of a hydrocolloid polymer is sodium alginate. In some embodiments, the cross-linking agent is a calcium salt. Examples of cross-linking agent includes, but is not limited to, calcium lactate, calcium butyrate, calcium chloride, calcium sulfate, calcium carbonate, calcium acetate, or calcium ascorbate.

In some embodiments of the presently disclosed subject matter, examples of the substrate includes, but is not limited to a pellet or a chewable for oral consumption. In some embodiments, the substrate includes a pellet, a chewable, a bead and a powder. In some embodiments, the substrate is an animal bait for enticing consumption. In some embodiments, the substrate comprises a plant-based or earthen-based substance. In some embodiments, the earthen-based substance includes but is not limited to soil or water. In some embodiments, the composition is a microencapsulated bead.

In some embodiments, the bioactive agent is a recombinant whole-cell bacteria engineered to express one or more antigens. In some embodiments, the whole-cell bacteria includes preparations of *E. coli*, while in other embodiments, the whole-cell bacteria includes, but is not limited to, a *Lactobacillus*, which includes *L. acidophilus*, *L. brevis*, *L. casei*, *L. crispatus*, *L. fermentum*, *L. gasseri*, *L. plantarum*, *L. reuteri*, *L. rhamnzosus*, and *L. salivarius*. In some embodiments, the whole-cell bacteria comprises a gram-negative bacteria. In some embodiments, the bacteria comprises *Escherichia coli*. In some embodiments, the one or more antigens are one or more *Borrelia burgdorferi* antigens.

Further provided, in some embodiments, the substrate is in an amount of about 85% to about 99% w/w of the composition. In some embodiments, the substrate is about 85%, 86%, 87%, 88%, 89%, 90%, 91%, 92%, 93%, 94%, 95%, 96%, 97%, 98% and about 99% w/w of the composition of the presently disclosed subject matter. In some embodiments, the microencapsulated bead is 100% of the composition. In some embodiments, the osmotic preconditioner is in an amount of about 0.2% to about 2% v/v of the stabilizer. The osmotic preconditioner is about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and about 2.0% of the stabilizer. In some embodiments, the stabilizer is in an amount of about 1% to about 15% w/w of the composition. The stabilizer is about 1%, 2%, 3%, 4%, 5%, 6%, 7%, 8%, 9%, 10%, 11%, 12%, 13%, 14%, and about 15% w/w of the composition as disclosed herein.

In some embodiments, the effective amount of the bioactive agent is an immunogenically effective amount with the minimal immunizing dosage (MID) of about $5\times10^3$ CFU to about $5\times10^7$ CFU. In some embodiments, the MID is about $5\times10^3$ CFU, $5\times10^4$ CFU, $5\times10^5$ CFU, $5\times10^6$ CFU, and about $5\times10^7$ CFU.

In some embodiments, cross-linking agent is in an amount of about 0.5% to about 7.5% w/w of the composition. The cross-linking agent is about 0.5%, 1%, 1.5%, 2%, 2.5%, 3%, 3.5%, 4%, 4.5%, 5%, 5.5%, 6%, 6.5%, 7%, and about 7.5% w/w of the composition. Further, in some embodiments, the coating is in an amount of about 1.5% to about 22.5% w/w of the composition. The coating is about 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, and about 22.5% of the composition as disclosed herein.

In some embodiments, the cross-linking agent is applied to the surface of the substrate from about 1 second to about 60 seconds after application of at least one bioactive agent. The time between the application of the bioactive agent and the cross-linking agent is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and about 60 seconds.

Further provided, in some embodiments of the presently disclosed subject matter, is a composition for oral delivery of a bioactive agent. The composition includes a substrate, an effective amount of at least one bioactive agent, and a cross-linking agent as described herein.

Still further, in some embodiments, a method of preparing a composition for oral delivery of a bioactive agent is provided. In some embodiments, the method includes the steps of osmotically preconditioning the at least one bioactive antigenic agent expressing the at least one antigenic agent, stabilizing at least one bioactive antigenic agent in a stabilizer, coating the stabilized at least one bioactive antigenic agent on to a substrate, and applying a cross-linking agent. In some embodiments, the cross-linking is used to facilitate gelation or encapsulation of the at least one bioactive antigenic agent. In some embodiments, the method further comprises the step of drying under forced air at an ambient temperature in a range of between about 20° C. to about 35° C. In some embodiments, the temperature is in a range of between about 20° C. to about 35° C., the temperature is about 20° C., 21° C., 22° C., 23° C., 24° C., 25° C., 26° C., 27° C., 28° C., 29° C., 30° C., 31° C., 32° C., 33° C., 34° C., and about 35° C. In some embodiments, a fan drives the ambient temperatures. In some embodiments, the method further includes a step of coating with a confectionary glaze layer on the exterior surface for moisture barrier or flavored attractant. In some embodiments, the method further includes a step of coating with a shellac layer on the exterior surface for moisture barrier.

The presently disclosed subject matter, in some embodiments, provides a method of controlling zoonotic infectious diseases by vaccinating a subject in need thereof. The method includes orally administering to the subject a composition as disclosed herein.

Further provided, in some embodiments, is a method of controlling zoonotic infectious diseases by vaccinating a subject in need thereof. The method includes orally administering to the subject a composition. The composition includes an effective amount of at least one bioactive agent layered over the substrate, wherein the at least one bioactive agent is stabilized in a stabilizer under conditions facilitating anhydrobiosis, and a cross-linking agent.

The presently disclosed subject matter, in some embodiments, provides a method of controlling zoonotic infectious diseases by vaccinating a subject in need thereof. The method comprises adding a composition directly to a water supply in a suspension suitable for drinking. The composition includes an effective amount of at least one bioactive agent layered over the substrate, wherein the at least one bioactive agent is stabilized in a stabilizer under conditions facilitating anhydrobiosis, and a cross-linking agent.

In some embodiments, the subject is a reservoir host of the zoonotic infectious disease cycle. In some embodiments, the subject is a susceptible host of the zoonotic infectious disease. In some embodiments, the subject is a xenodiagnostic carrier. In some embodiments, the subject is an arthropod or insect. In some embodiments, the subject is a mammal. In some embodiments, the mammal is a feral animal includes one or more of a mouse, a chipmunk, a squirrel, a shrew, a vole, a rat, a raccoon, an opossum, a skunk, a rabbit, and a deer. In some embodiments, the subject is a bird. In some embodiments, the subject is fish. In some embodiments, the subject is a domesticated or companion animal. In some embodiments, the domesticated animal comprises one or more of a dog, a cat, a cow, and a horse.

Advantages of the presently disclosed subject matter will become evident to those of ordinary skill in the art after a study of the description, Figures, and non-limiting Examples in this document.

BRIEF DESCRIPTION OF THE DRAWINGS

FIG. 3 is an image of the results of sequencing analysis of plasmid-vectored ospA in the forward direction.

FIG. 4 is an image of the results of sequencing analysis of plasmid-vectored ospA in the reverse direction.

FIG. 7 is a diagram showing vaccine coating, crosslinking, and layering process.

BRIEF DESCRIPTION OF THE SEQUENCE LISTING

Figure 1:
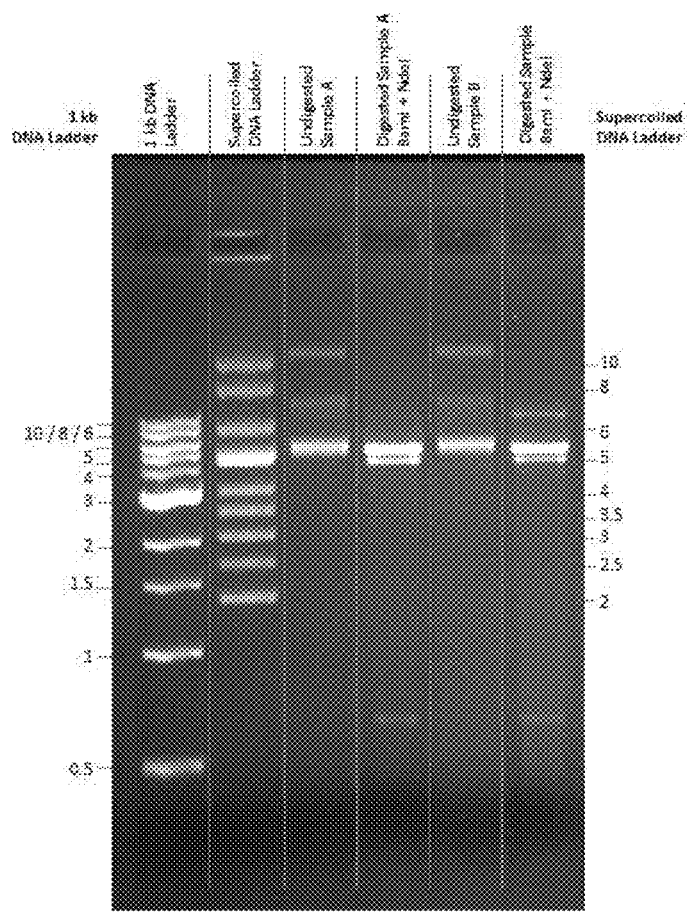
FIG. 1 is an image of a restriction digest of pET9c plasmid vectored ospA.
Figure 2:
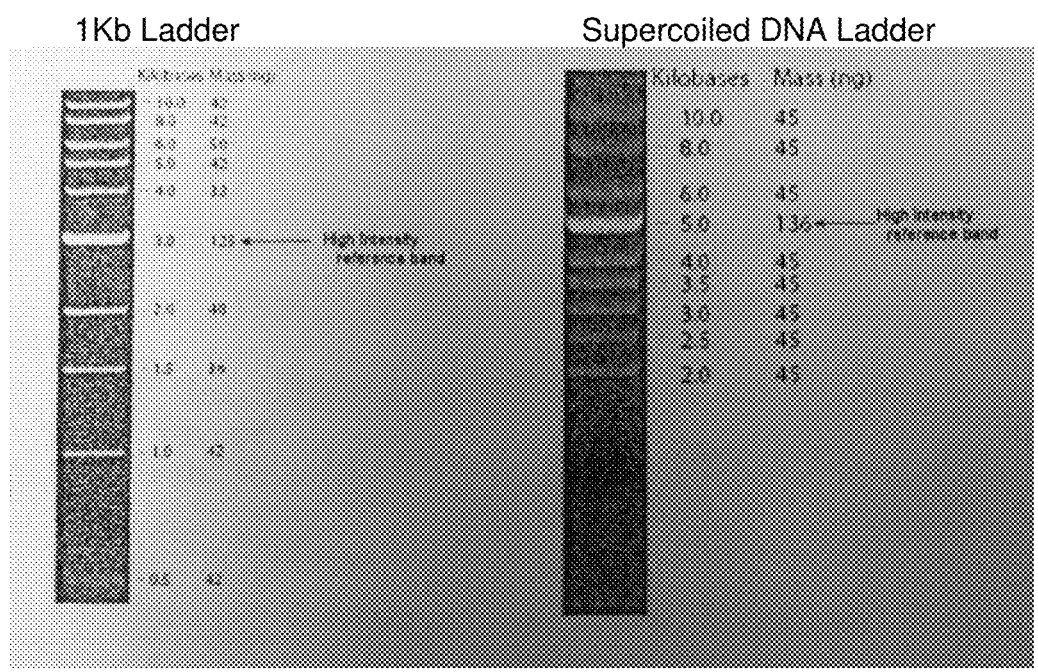
FIG. 2 is an image of DNA base-pair ladder standards.

The instant application contains a Sequence Listing which has been submitted electronically in ASCII format and is hereby incorporated by reference in its entirety. Said ASCII copy, created on Nov. 25, 2020, is named M_USBIO002DIV.txt and is 2.36 bytes in size.

SEQ ID NO: 1 is T7 Promoter Primer sequence.
SEQ ID NO: 2 is T7 Terminator Primer sequence.
SEQ ID NO: 3 is a nucleic acid sequence of ospA gene reference sequence.
SEQ ID NO: 4 is flaB gene Forward Primer sequence.
SEQ ID NO: 5 is flaB gene Reverse Primer sequence.

Description of Exemplary Embodiments

The details of one or more embodiments of the presently disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

While the terms used herein are believed to be well understood by one of ordinary skill in the art, definitions are set forth herein to facilitate explanation of the presently disclosed subject matter.

Unless defined otherwise, all technical and scientific terms used herein have the same meaning as commonly understood by one of ordinary skill in the art to which the presently disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently disclosed subject matter relates to a composition and method of using the composition for oral delivery of a biologically active agent to a subject. More particularly, the presently disclosed subject matter relates to a composition comprising a substrate and an effective amount of at least one biologically active agent stabilized by layered encapsulation over the substrate and a method of reducing zoonotic infectious disease by administering the composition to a subject. The presently disclosed subject matter further relates to a method of preparing the composition.

In some embodiments of the presently disclosed subject matter, a composition is provided. The composition includes a substrate, an effective amount of an osmotically preconditioned at least one bioactive agent layered over the substrate, and a cross-linking agent. In some embodiments, the at least one bioactive agent is stabilized in a stabilizer under conditions facilitating anhydrobiosis.

The term "bioactive agent," "biologically active agent," and "bioactive antigenic agent" refers to any substance that is of medical or veterinary therapeutic, prophylactic or diagnostic utility. In some embodiments, the bioactive agent includes a therapeutic agent. As used herein, a therapeutic agent refers to a bioactive agent that, when administered to a patient, will cure, or at least relieve to some extent, one or more symptoms of, a disease or disorder. In some embodiments, bioactive agent includes a prophylactic agent. As used herein, a prophylactic agent refers to a bioactive agent that, when administered to a patient either prevents the occurrence of a disease or disorder or, if administered subsequently to a therapeutic agent, prevents or retards the recurrence of the disease or disorder. In some embodiments, bioactive agent refers to antigens that elicit an immune response, or proteins that can modulate the immune system, to enhance therapeutic potential. In some embodiments, the administration of the biologically active antigenic agent can elicit an immune response that is either prophylactic to prevent disease contraction and transmission, or therapeutic to resolve existing disease infection.

In some embodiments, the bioactive agent comprises a recombinant whole-cell bacteria engineered to express one or more antigens. As used herein, "whole-cell bacteria" refers to bacterial cells, maintained under conditions that retain the bacterial cellular structural integrity, that is, whole-cell structural integrity and antigenicity, as a bioactive recombinant exogenous protein expression system vehicle for the stable presentation of antigen in certain embodiments. Conditions favorable for the structural integrity of the bioactive agent is defined as "stabilized." In certain embodiments, whole cells will be maintained as stable, not to be broken down into cellular fragments and/or other biological material and/or organelles. In maintaining the stabilized whole-cell structural architecture, some embodiments may encompass "active formulations," defined as live whole-cell bacterial units; other embodiments may encompass "inactive formulations," defined as killed whole-cell bacterial units termed bacterins.

In some embodiments, the whole-cell bacteria includes anhydrobiotic preparations of *E. coli*, while in other embodiments, the whole-cell bacteria includes, but is not limited to, a *Lactobacillus*, which includes *L. acidophilus, L. brevis, L. casei, L. crispatus, L. fermentum, L. gasseri, L. plantarum, L. reuteri, L. rhamnzosus,* and *L. salivarius*. In some embodiments, the whole-cell bacterial is a recombinant bacteria engineered to express one or more antigens. In some embodiments, the recombinant bacteria are engineered to express at least one outer surface protein of *Borrelia burgdorferi* for use as Lyme disease vaccines. (See U.S. Pat. No. 8,821,893, which is incorporated herein by reference in its entirety). In some embodiments, the recombinant bacteria are lyophilized/freeze-dried.

As used herein, the bioactive agent, or biologically active agent, comprises a whole-cell bacterial antigenic expression vehicle. As used herein *Escherichia coli* is used as an Antigenic Expression Vehicle.

The use of biological vehicles (biologics) as prophylactic and/or therapeutic intervention strategies in the control of disease has increased recently given the application of recombinant expression technologies. As a biologic, *Escherichia coli* is a biotechnology-qualified whole-cell bacterial protein expression system. *E. coli* are easily transformed and can be engineered for induced (controlled) expression of recombinant proteins. Such exogenous protein expression further lends qualification to the use of *E. coli* as a vehicle for presentation of antigen in the context of a vaccine carrier. Additionally, *E. coli*, as used in the presently disclosed subject matter, is a commensal microorganism and presents as a favorable and effective vehicle for oral vaccine administration and presentation of antigen to the mucosal-associated lymphatic tissue of the gastrointestinal (GI) tract.

In some embodiments, the composition disclosed in the present application further includes an adjuvant. As used herein, the term "adjuvant", or "adjuvantized", will refer to any material capable of enhancing a vaccine-induced immune response in an animal. In some embodiments, compositions embodying whole-cell bacterial units, molecularly engineered antigenic fusion proteins, or biochemical immunomodulators present as natural adjuvants. Whole *E. coli* bacterial cell units are immunogenically reactive through the presentation of lipopolysaccharide (LPS); LPS is a ligand for activating the Toll-like receptor 4 (TLR4), essential for the immuno-surveillance of Gram-negative bacterial infections and the activation of the innate immune system (Flanagan et al., J. Endotoxin Res. 6:481, 1996). The amino-terminal 22 amino acids of OspA account for the lipidated moiety of the protein (the OspA lipoprotein) and presents as a natural immunogenic hydrophobic signal peptide capable of the induction of pro-inflammatory cytokines (Erdile et al., Infect. Immun. 61:81, 1993). In some embodiments, the OspA lipoprotein can be fused in-frame and proximal with other antigenic proteins as an expressed molecular adjuvant fusion protein construct. Preparations employing the use of cholera toxin (CT), when mixed with the whole *E. coli* bacterial cell units serve as a potent biochemical immunomodulators on enteric mucosal immune responses (Bowman and Clements, Infect. Immun. 69:1528, 2001).

Under specific induction conditions of liquid culture, as that which is used in the presently disclosed subject matter, *E. coli* expand exponentially and, while hydrated, produce a stable bulk expressed protein of a potent product yield. However, while an ideal recombinant protein expression system, *E. coli* are non-spore-forming (sensitive to desiccation), are not biologically stable once harvested from culture, and therefore do not effectively present as stable vehicles supporting the biologistic challenges associated with the storage (shelf life stability), delivery (environmental stability), administration (enteric stability), and efficacy (antigenic potency and stability) required of biologic-based vaccines. As used in the presently disclosed subject matter, the induction of anhydrobiosis is defined as a biologically stable state of desiccation, and as used herein is therefore a downstream bio-processing step introduced during production as a means to stably dry the biologic product to facilitate and accommodate the subsequent biologistics requirements.

Currently employed strategies for bulk anhydrobiotic processing include lyophilization (freeze-drying) of the biologic product resulting in a physical powder. However, the process of lyophilization results in a significant loss of potency to E. coli as a whole-cell antigen expression vehicle. Further, lyophilization is not easily scalable and can be costly for industrial application; as a powder, the resultant product must be further formulated for stability, application and administration as a vaccine.

Additional anhydrobiotic processing strategies have involved the use microencapsulation technologies for entrapping biologics in spheronized microbeads. Such technologies are employed in the processing of lactic acid bacteria (LAB) for use in the probiotics industry. However, LAB are generally less efficient vehicles for recombinant protein expression, and thereby may not present as potent or efficacious vaccines. Further, the employment of downstream processing that results in the generation of microencapsulated biologics in the form of spherical microbeads, a product that presents as a course powder of beads the size of which may range from 100 µm to several thousand µm, may not be of a size practical for targeted distribution as a reservoir targeted vaccine. Such beads are also of a composition of cellulose, specifically microcrystalline cellulose (MCC), a composition that may not be favorable for targeted (attractive) consumption as a bait by reservoir hosts.

Further to the above, stability measures supporting oral administration of biologics employ the use of enteric protection for effective passage through the gut for specific release at targeted regions of the GI tract. The introduction of enteric stabilization methodologies has been utilized with success in the probiotics industry for administering efficacious doses of LAB as part of a regimen for enhancing the gut microbiome and systemic health. Current strategies employ calcium-alginate encapsulation chemistries, wherein a given concentration of polymeric matrix comprising the probiotic in composition with a solution of alginate are dripped via vibrational nozzle, or spray atomized, into a bath of a given concentration of a calcium salt facilitating a cross-linking (microencapsulation) of the polymeric matrix. The resultant microencapsulated probiotic product is retrieved from the calcium bath and subsequently lyophilized yielding the powdered final product for consumption. However, and as presented above, powdered formulations of biologics must be further downstream processed and formulated for application as RTVs. Powders will need to be applied with uniformity, for quality analysis standardization, as layers onto baiting substrate options. Such application may require added liquid carriers, drying measures, or physical applications to accommodate powders, all of which may be of detriment to the potency, and consequently, the efficacy of the said vaccine vehicle.

Reservoir targeted vaccines must target the susceptible reservoir host of the disease that is part of the enzootic disease cycle. Consequently, a baiting material of a size that promotes targeted consumption, at a scale that accommodates a mass targeted wildlife distribution campaign, must be employed as an attractant for the reservoir host. This baiting material, the substrate of which is summarized in the presently disclosed subject matter, is also a carrier for the administration of an orally delivered, reservoir targeted vaccine.

Inclusion of the vaccine vehicle within the context of the reservoir targeted bait substrate requires a formulation that extends stability to the *E. coli* antigenic expression vehicle. The E. coli-based vehicle is sensitive to heat and pressure rendering the biologic ineffective if formulated as an amalgam in composition, and extruded, with the substrate.

A composition and method is needed for the stable presentation of antigen, in the context of a whole-cell bacterial vehicle, and administered in the context of a carrier substrate, as a reservoir targeted vaccine for the control of zoonotic disease.

Specifically, a need exists where the passage and culture of the *E. coli* antigenic vehicle remains under a specific induction condition to maintain a controlled, and less toxic level of antigenic expression.

There is also a need for a unique downstream processing protocol that accommodates the unique biologic nature of the E. coli antigenic vehicle as a means to osmotically precondition the vehicle for anhydrobiosis. As part of this preconditioning protocol, there is a need for establishing the composition and methods for the vehicle preconditioning process, to include the stability carrier matrix formulation and temperature parameters, and the subsequent application of the carrier matrix upon the carrier substrate.

Finally, as part of the process for stabilizing *E. coli*-based vaccine vehicles for oral administration, there exists a need for enteric stability for effective presentation of the vaccine antigen to specific regions of the gut of the reservoir host.

In certain embodiments, the composition comprises a substrate and an effective amount of at least one bioactive antigenic agent coated or layered over the substrate. As used herein, the term "substrate" refers to a solid support composition, such as a carrier, onto which may be applied the stabilized vaccine composition.

In some embodiments, non-limiting examples of the bioactive antigenic vaccine agent include whole-cell bacteria as a biological vehicle of the antigenic agent. In some embodiments, the bioactive antigenic agent is osmotically pre-conditioned for anhydrobiosis and stabilization. As used herein, the term "osmotically preconditioned" refers to the use of specific solutes employed to physically stabilize and protect membranes and proteins in intact bacteria prior to drying to desiccation. Non-limiting osmotic preconditioners include plasticizing agents such as sugars, to include sucrose and/or trehalose, or hydroxyectoine. As used herein, the term "anhydrobiosis" refers to the physical state of biological tolerance to desiccation. Biological desiccation serves to maintain a biologically active composition, without water, thereby enhancing shelf life stability for extended vaccine potency.

In some embodiments, the bioactive antigenic agent is stabilized in a stabilizer. Stabilization refers to the means of promoting and maintaining the biological activity of the bioactive antigenic agent, wherein the whole-cell antigenic carrier is structurally maintained for effective presentation of antigen as an immunogen. Non-limiting stabilizers incorporate the use of hydrocolloids. As used herein, the term "hydrocolloid" will refer to any material of the colloid family of hydrophilic polymers dispersed in aqueous solution. Hydrocolloids present, in some embodiments, as small particles of about 1 to about 1000 nm in diameter, and serve to encapsulate and stabilize biological material. A hydrocolloid of the present disclosure may include, but is not limited to, agar, alginate, carrageenan, chitosan, gelatin, and/or gum.

Suitable hydrocolloids may include one or more natural and synthetic polymers, which form colloidal solutions in aqueous systems. Preferable hydrocolloids include polysaccharides, such as alginic acid, sodium alginate, and calcium alginate. Suitable hydrocolloids include polyvinyl pyrrolidones; starch; cellulose and cellulose derivatives, such as ethylcellulose, methyl cellulose, hydroxypropylmethyl cellulose (HPMC), hydroxypropyl cellulose (HPC), and carboxymethylcellulose; (CMC); polyethylene glycol (PEG); or mixtures thereof.

In some embodiments, certain hydrocolloid polymers, such as sodium alginate, may be cross-linked in the presence of a calcium salt. Cross-linking in the presence of a divalent cation such as calcium refers to the capacity to structurally link the polymeric bonds of the hydrocolloid polymer, sodium alginate, to calcium to generate a polymer of calcium alginate cross-linked bonds; calcium ions replace the sodium ions in the alginate polymer yielding what is termed polymerization. Polymerization via cross-linking facilitates the stabilized encapsulation of the active vaccine agent as used in the presently disclosed subject matter.

In some embodiments, the cross-linking agent is a calcium salt. Examples of cross-linking agent includes, but is not limited to, calcium lactate, calcium butyrate, calcium chloride, calcium sulfate, calcium carbonate, calcium acetate, or calcium ascorbate. As used in the presently disclosed subject matter, the cross-linking agent facilitates polymerization of the stabilizer.

As presented herein the composition of the presently disclosed subject, the composition relates to a composition comprising a substrate and an effective amount of at least one biologically active antigenic agent stabilized by layered encapsulation over the substrate. As used herein, the term substrate relates to a substance of solid support, suitable for oral consumptions, upon which or around which (as a shell or coating) may be applied the osmotically preconditioned stabilized at least one bioactive antigenic agent.

In some embodiments, the substrate has a mean diameter of from about 100 μm to about 2 cm. In some embodiments, the composition may be of a range of size about 2 cm (as in pellets) to accommodate consumption by target animal species.

In some embodiments of the presently disclosed subject matter, examples of the substrate include, but is not limited to, pellet, a chewable, a bead and a powder. In some embodiments, the substrate comprises a plant-based or earthen-based substance. In some embodiments, the earthen-based substance includes but is not limited to soil or water.

In some embodiments, the substrate is of a collective composition that is an electrosprayed microencapsulated bead.

In some embodiments, the substrate further includes, but is not limited to, a plant and/or forage material to include grass, herbaceous legumes, tree legumes, silage, or crop residues to include grains such as corn or soybean stover, or other earthen-based substance, such as soil, compost, or addition directly to water. In certain embodiments, the substrate is edible, and appropriate to be fed to animals in a composition with a vaccine formulation. In some embodiments, the substrate may comprise a dried pellet or kibble, such as a particle generated by compressing original material, which may be broken up upon mastication into particulate material; and/or a chewable particle, soft and pliable in nature, such that it is not readily broken up or reduced to particulate matter upon mastication but may be readily dissolved; micro-crystalline cellulose beads or other substrate for employment in the generation and application of vaccine in powdered formulation for administration via nasal inhalation, or to be administered directly to water as a hydrocolloidal suspension as an oral administration via drinking; a plant; a food-source, such as a food source that is available in the wild; and/or another earthen substance, soil or other onto which may be applied the active vaccine composition, which is then dried for stability, or water into which may be applied the active vaccine composition for consumption by drinking.

In some embodiments, the composition further includes a coating on the exterior surface of the composition. In some embodiments, the coating on the exterior surface is a shellac coating. In some embodiments, the coating is an enteric coating. In some embodiments, the coating on the exterior surface of the substrate is sequentially applied in layers as a top-dressing and comprises an enteric coating once cross-linked.

In some embodiments, the substrate is in an amount of about 85% to about 99% w/w of the composition. In some embodiments, the stabilizer is in an amount of about 1% to about 15% w/w of the composition. In some embodiments, the effective amount of the bioactive agent is an immunogenically effective amount with the minimal immunizing dosage (MID) of about $5\times10^3$ CFU to about $5\times10^7$ CFU. In some embodiments, cross-linking agent is in an amount of about 0.5% to about 7.5% w/w of the composition. Further, in some embodiments, the coating is in an amount of about 1.5% to about 22.5% w/w of the composition.

Further, regardless of the particular mode and timing of administration used in accordance with the methods of the presently disclosed subject matter, the bacterium, including the bacterium-based compositions and antigenic agents described herein, are typically administered in an amount effective to achieve the desired response (i.e., protection against the antigenic agents). As such, the term "effective amount" is used herein to refer to an amount of the therapeutic composition sufficient to produce a measurable biological response (e.g., an immune response against *Borrelia* burgdorferi infection). In this regard, in some embodiments, the term "therapeutically effective" is used interchangeably herein with the phrase "immunogenically effective" to refer to an amount of whole-cell bacterial vehicle expressing the at least one or more antigenic agent of the presently-disclosed subject matter sufficient to induce an effective immune response in a host against a virulent bacterium. Actual dosage levels of active ingredients in a therapeutic composition of the presently disclosed subject matter (e.g., the bacterium) can be varied so as to administer an amount of a composition that is effective to achieve the desired therapeutic response for a particular subject and/or application. Of course, the selected dosage level and amount of the bacterium and the other components of such a composition will depend upon a variety of factors including the activity of the bacterium, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art. As used herein, for example, in some embodiments, the therapeutic effective dose of the at least one antigenic agent is of a minimum immunizing dosage (MID) as measured in active antigen-expressing colony forming bacterial units (CFU) of about $5 \times 10^3$ to about $5 \times 10^7$ CFU.

In some embodiments of the presently disclosed subject matter, a composition for oral delivery of a bioactive agent is provided. The composition includes a substrate, an effective amount of at least one bioactive agent coated or layered on a substrate, and a cross-linking agent to facilitate the encapsulation of the antigenic in the stabilizer on the surface of the substrate. In some embodiments, the at least one bioactive agent is stabilized in a stabilizer selected from a group consisting of a hydrocolloid polymer further comprising a plasticizing sugar to include sucrose or a trehalose. In some embodiments, the bioactive agent is an antigenic agent.

Still further, in some embodiments, a method of preparing a composition for oral delivery of a bioactive agent is provided. The method includes the steps of uniquely passaging and culturing the at least one antigenic agent; osmotically preconditioning the at least one antigenic agent; stabilizing at least one antigenic agent in a stabilizer; coating the stabilized at least one antigenic agent on to a substrate; applying a cross-linking agent; cross-linking to facilitate gelation or encapsulation of antigenic agent; and drying under forced air at an ambient temperature. In some embodiments, the temperature is in a range of between about 20° C. to about 35° C. In some embodiments, a fan drives the ambient temperatures. In some embodiments, the methods further include a step of coating with a confectionary glaze layer on the exterior surface for moisture barrier or flavored attractant. In some embodiments, the method further includes a step of coating with a shellac layer on the exterior surface for moisture barrier.

Current methods for generating calcium-alginate encapsulated biological materials require the generation of hydrogel or calcium-alginate beads. Bead-encapsulated biological materials are generated by the pressurized dispensing of sodium alginate into a volume of calcium salt, a process employing specific encapsulation equipment (an encapsulator) (Mazzitelli et al., *J. Biomat. Appl.* 23:123, 2008). Calcium-alginate beads generated by an encapsulator can be harvested and dried for downstream application. The bead format does not render itself beneficial or efficient for the uniform application onto defined substrates for targeted distribution and administration. Id.

Examples of encapsulation of antigens for oral administration include the following issued patents. For example, U.S. Pat. No. 5,352,448 describes the formulation and generation of hydrogels that can be loaded with antigen for oral administration as a hard, glassy bead. Additionally, U.S. Pat. No. 5,900,238 similarly describes the formulation and generation of antigen-encapsulated hydrogel microbeads for mucosal vaccination. Further examples include WIPO Pat. No. WO 2013/096883, which presents the methods for generating a spray-dried microencapsulated biological moieties and chemicals in polymers cross-linked by multivalent ions.

The presently disclosed subject matter provides a method of preparing a composition for oral delivery of a biologically active antigenic agent. The method includes, for example, the steps of: stabilizing by osmotic conditioning at least one antigenic agent, coating the at least one antigenic agent onto a substrate employing a sodium alginate suspension as a liquid carrier for layered application, cross-linking by a secondary layering of a calcium salt to facilitate layered gelation via calcium-alginate encapsulation of the antigenic vehicle, and air drying under forced air ambient temperatures yielding a layered anhydrobiotic preparation of the biologically active antigenic agent. In some embodiments, the methods of the present disclosure include a step of coating the antigenic vehicle and/or the substrate with a glaze layer on the exterior surface to provide a moisture barrier and/or flavored attractant. Further, in some embodiments, the methods of the present disclosure include a step of coating a shellac layer on the exterior surface of the antigenic vehicle and/or of the substrate to provide a moisture barrier. As such, employment of the more simplified sequential spray coating and layering application of the encapsulated biological materials provides an efficient and commercially viable method for the applying stabilized biologically active materials as layered coatings over a substrate. Encapsulated layering onto substrates provides a carrier method for targeted distribution of the biologically active agent.

In some embodiments, the presently disclosed subject matter relates to composition and methods for the stable expression of antigens for mucosal administration, more particularly, relates to oral administration to a subject such as a mammal.

In some embodiments of the presently disclosed subject matter, the active vaccine agent is passaged in TBY media (tryptone broth with yeast extract, with kanamycin selective agent at 50 µg/ml) at 35° C.±2° C. under constant agitation until $OD_{600}$ nm=0.8. In some embodiments of the presently disclosed subject matter, the active vaccine agent is cultured in induction media (Overnight Express™ Instant TB Medium, Merck-Millipore Catalog #71491, used under license, with kanamycin selective agent at 100 µg/ml) at 30° C.±2° C. under constant agitation until $OD_{600}$ nm=1.5±0.2, to generate the induced (expressed antigen) biomass. As used in the presently disclosed subject matter, the biomass is washed free of culture fluids by suspension in phosphate-buffered saline (PBS; 0.8% Sodium Chloride, 0.02% Potassium Chloride, 0.144% Sodium Phosphate Dibasic, 0.024% Potassium Phosphate Monobasic).

In some embodiments of the presently disclosed subject matter, the active vaccine agent is osmotically preconditioned at 4° C. in about 500 mM to about 625 mM sucrose and/or about 500 mM to about 625 mM hydroxyectoine, dissolved in PBS. Pre-conditioned active agent is then mixed into a matrix of about 1.0% to about 1.5% sodium alginate in suspension with about 500 mM to about 625 mM sucrose, which is then applied onto the surface of the substrate by spray coating. A secondary layering of about 60 mM to about 225 mM concentration of a calcium salt is applied onto the surface of the substrate by spray coating. In some embodiments, the secondary layer is applied to the surface of the substrate about 1 second to about 60 seconds after application of the first layer. As used in the presently disclosed subject matter, the calcium salt is calcium lactate. In some embodiments, the calcium salt can be calcium butyrate, calcium chloride, calcium sulfate, calcium carbonate, calcium acetate, or calcium ascorbate.

As used herein, the term "shellac" refers, in some embodiments, to an external edible glaze, resin, and/or coating applied externally to a vaccine-coated substrate. In some embodiments, a shellac coating comprises a moisture barrier that is useful, for example, in the deployment of an orally administered vaccine, enhancing the vaccine shelf life and stability.

The presently disclosed subject matter, in some embodiments, provides a method of controlling zoonotic infectious diseases by vaccinating a subject in need thereof. The method includes orally administering to the subject a composition as disclosed herein. In some embodiments, the presently disclosed subject matter relates to a method of orally administered biological-based vaccines utilizing antigen-expression systems comprising vectored bacteria that, upon consumption, elicit an immune response in targeted mammalian populations.

The present disclosure also relates to methods of stabilizing the active biological agent/component of a vaccine such that antigenic activity may be preserved and measured as a dosage; that the dosage maintains antigenicity for absorption by the immunologically-active GALT (gut-associated lymphoid tissue) or NALT (naso-pharyngeal-associated lymphoid tissue); and that the immunological response yields a reaction to the vaccine that is sustained, measurable, and prophylactic or therapeutic in the level of sero-responsiveness as assayed by antibody titers. Antibody titers are transmissible as prophylactically active compounds to neutralize targeted zoonotic incidence of infection.

Related to a methods of use for the presently disclosed subject matter, animal mucosal surfaces present as principle entry sites for many infectious agents. Consequently, mucosal immunity offers an initial line of defense against infectious agents. The mucosal immune response interferes with the infectious process by hindering pathogen attachment to the mucosal epithelium, neutralizing viral and bacterial agents, and providing the means by which to remove pathogens through phagocytosis. The mucosal-associated immune system functions to prevent microbial penetration and infection through the internal regions of the animal. Because of the extensive immunological nature associated with the mucosal immune system, the region is also effectively targeted for vaccine administration to elicit prophylactic immunoresponsiveness against several pathogens (Chen and Cerutti, *Immunity* 33:479, 2010; Fujkuyama et al., *Expert Rev. Vaccines* 11:367, 2012; Neutra and Kozlowski, *Nature Rev. Immunol.* 6:148, 2006; Ogra et al., *Clin. Microbiol. Rev.* 14:430, 2001; Woodrow et al., *Annu. Rev. Biomed. Eng.* 14:17, 2012).

The local immune response is most effectively induced in response to direct application of antigens to the mucosal surface. The site-specific presentation of antigens in native conformation, however, presents a challenge in terms of the available administrative carrier vehicles and the toxicity associated with the antigens. Therefore, local immunity may be induced via the stimulation of the mucosa-associated lymphoid tissue (MALT), an integrated network of immunologically active mucosal tissue. Exposure by antigen at the mucosal surfaces of the gut or lung triggers the complex migration of lymphocytes to all mucosal regions where production of antigenic-responsive antibodies is produced. Antigenic exposure further induces a population of memory lymphocytes, which serve to generate antibodies in response to subsequent exposure by the same antigen. Hence, the MALT presents as a target for effective vaccination, by triggering the local immune response (Chen and Cerutti, *Immunity* 33:479, 2010; Fujkuyama et al., *Expert Rev. Vaccines* 11:367, 2012; Neutra and Kozlowski, *Nature Rev. Immunol.* 6:148, 2006; Ogra et al., *Clin. Microbiol. Rev.* 14:430, 2001; Woodrow et al., *Annu. Rev. Biomed. Eng.* 14:17, 2012).

Of the immunologically active mucosal surfaces, the MALT of the gut-associated lymphoid tissues (GALT) in the intestines presents with the greatest accumulation of lymphoid tissue. GALT contains populations of functional T and B lymphocytes in conjunction with antigen-presenting accessory cells. Specifically, the B lymphocyte population of the GALT comprises a significant subset of cells committed to the generation of the immunoglobulin A (IgA) class of antibodies. As a neutralizing antibody, the localized availability of IgA of the GALT provides an effective means of preventing invading pathogens from attaching and penetrating the epithelial layer of the mucosal surfaces. This form of immunoresponsiveness differs from that of the systemic lymphoid tissues where the IgA antibody class is not effectively induced through the conventional intramuscular (IM) or subcutaneous (SubQ) methods of immunization administration (Chen and Cerutti, Immunity 33:479, 2010; Fujkuyama et al., *Expert Rev. Vaccines* 11:367, 2012; Neutra and Kozlowski, *Nature Rev. Immunol.* 6:148, 2006; Ogra et al., *Clin. Microbial. Rev.* 14:430, 2001; Woodrow et al., *Annu. Rev. Biomed. Eng.* 14:17, 2012).

An epithelial cell layer of the GALT separates the underlying lymphoid layer of the mucosa from the lumen of the gut. Interspersed within the epithelial layer are accessory cells with a committed function for antigen presentation. Such accessory cells actively sample luminal antigenic samples, internalizing the samples for processing and presentation to the adjacent lymphoid cells. Presentation and exposure of antigen to the GALT initiates the clonal expansion of antigen-specific B and T lymphocytes. The IgA-committed B lymphoblasts consequently migrate through the roesenteric lymph nodes, by means to trigger an enhanced specific immune response in all mucosal sites, including the intestinal tract, nasopharyngeal and respiratory tracts, lung, oral cavity, ocular regions, mammary gland, and genitourinary tract. Therefore, immuno-stimulation of the GALT through oral vaccination may consequently result in the prevention of infectious diseases at a variety of mucosal surfaces (Chen and Cerutti, *Immunity* 33:479, 2010; Fujkuyama et al., *Expert Rev. Vaccines* 11:367, 2012; Neutra and Kozlowski, *Nature Rev. Immunol.* 6:148, 2006; Ogra et al., *Clin. Microbiol. Rev.* 14:430, 2001; Woodrow et al., *Annu. Rev. Biomed. Eng.* 14:17, 2012).

In accordance with an embodiment of the present disclosure, animals are vaccinated via oral administration with hydrocolloid-stabilized/encapsulated whole-cell vehicles coated onto edible delivery substrates.

Successful and efficacious orally administered vaccines require stability of the antigen as it passes through the digestive tract. As functional proteins dependent upon conformational structure, the configuration of antigens can be denatured under the digestive process of the gut. Enteric drug-delivery systems have been developed to protect the pharmaceutically active compounds for passage to the intestine. Moreover, hydrocolloids are useful for whole-cell encapsulation and/or for maintenance of cellular enzymatic reaction potential. In some embodiments of the present disclosure, hydrocolloids are, by virtue of their chemical and physical properties, employed as an enteric coating(s) for stabilizing the whole-cell antigen for effective presentation to the MALT. Hydrocolloids, such as alginates, offer a hydrophilic gel-network stabilization matrix that allow protection of encapsulated biologics for effective passage to targeted mucosal tissues, such as the GALT.

In some embodiments, the presently disclosed subject matter provides a method for effectively stimulating a mucosal immune response to presented antigen. Specifically, the present disclosure relates, in certain embodiments, to the use of hydrocolloid-stabilized biological vehicles, such as whole-cell bacteria, as vehicles for the expression of antigens in native conformation. This presently disclosed subject matter further relates to methods of complexing the stabilized biological vehicles in combination with compositions of substrates that facilitate delivery of the antigens to the mucosal-associated lymphoid tissues, via oral, and/or nasal administration.

Further provided, in some embodiments, is a method of controlling zoonotic infectious diseases by vaccinating a subject in need thereof. The method includes orally administering to the subject a composition. The composition includes an effective amount of at least one bioactive agent layered over the substrate, wherein the at least one bioactive agent is stabilized in a stabilizer under conditions facilitating anhydrobiosis, and a cross-linking agent.

The presently disclosed subject matter, in some embodiments, provides a method of controlling zoonotic infectious diseases by vaccinating a subject in need thereof. The method comprises adding a composition directly to a water supply in a suspension suitable for drinking. The composition includes an effective amount of at least one bioactive agent layered over the substrate, wherein the at least one bioactive agent is stabilized in a stabilizer under conditions facilitating anhydrobiosis, and a cross-linking agent.

In some embodiments, the presently disclosed subject matter provides an oral vaccine composition for reducing vector-borne and/or other zoonotic infectious diseases. As used herein, the term "zoonotic" or "zoonosis" refers to an infectious disease that may be transmitted between species. In some embodiments, infectious disease transmission may be facilitated by a disease-transmitting vector, to include, but is not limited to an insect (mosquito or other) and/or arthropod (tick or other). In some embodiments, zoonotic disease is vector-borne.

As used herein, "vectors" are living organisms that can transmit infectious diseases between humans or from animals to humans. Many of these vectors are bloodsucking insects, which ingest disease-producing microorganisms during a blood meal from an infected host (human or animal) and later inject it into a new host during their subsequent blood meal. In some embodiments, the vector-borne zoonotic disease is Lyme disease. "Vector-borne diseases" are illnesses caused by pathogens and parasites in human populations. Vector-borne and other types of zoonotic infectious disease include, but are not limited to Anaplasmosis, Babesiosis, Ehrlichiosis, Rocky Mountain Spotted Fever, Dengue, or Malaria.

In some embodiments of the presently disclosed subject matter, a method of controlling zoonotic infectious disease by vaccinating a subject in need thereof is provided. The method comprises orally administering to the subject a composition comprising a substrate and an effective amount of at least one active agent coated or layered over the substrate. In some embodiments, the subject is a reservoir host of the zoonotic infectious disease cycle. In some embodiments, the subject is a susceptible host of the zoonotic infectious disease cycle. In some embodiments, the subject is a xenodiagnostic carrier. Non-limiting examples of the subject include an arthropod, an insect, a mammal, a bird, a fish, and/or a domesticated or companion animal. In some embodiments, the mammal includes a feral animal including one or more of a mouse, a chipmunk, a squirrel, a shrew, a vole, a rat, a raccoon, an opossum, a skunk, a rabbit, and a deer. In some embodiments, the subject is a domesticated or companion animal. In some embodiments, the domesticated animal including one or more of a dog, a cat, a cow, and a horse. In some embodiments, the subject is a bird. In some embodiments, the subject is fish.

As used herein, the term "reservoir host" refers to an organism harboring infectious disease microorganisms or pathogens, but presenting as asymptomatic. Specifically, as referred to herein, the reservoir host serves in the transmission cycle of zoonosis by harboring infectious agents that may be transmitted to other reservoir hosts, or subsequent susceptible hosts. In some embodiments, a reservoir host may transmit an amount of an infectious agent to, for example, a feeding vector, which may be transmitted to a subsequent reservoir host and/or subsequent susceptible host.

As used herein, the term "susceptible host" refers to an individual organism that is predisposed, vulnerable, and/or receptive to disease. Specifically, as referred to herein, the susceptible host is receptive to the disease transmitted by a disease-harboring vector carrier. Specifically, as referred to herein, the term "xenodiagnostic carrier" may be employed to describe a diagnostic method to document the presence of infectious disease-presenting microorganisms, or pathogens, by exposing potentially infectious tissue to a naive vector, and then assaying the vector for the presence (ingested) of the same infectious agent(s).

The presently disclosed subject matter is further illustrated by the specific but non-limiting examples provided herein. Moreover, the following examples may include compilations of data that are representative of data gathered at various times during the course of development and experimentation related to the present disclosure.

Methods and results disclosed herein are provided to report an analysis of vaccine efficacy. An efficacious vaccine is defined as one that induces a sustained immune response based upon a designated administration protocol. Immunoresponsiveness is dependent upon the presentation of an antigen to the immune system. For the present disclosure, antigenic presentation considers the utility of a biological system, a maintained bacterial whole-cell vehicle whereby said antigen is stably expressed on the cell surface for effective presentation to the immune system upon administration. Bacterial expression systems further present as natural adjuvants for use in the enhancement of the vaccine-induced immune response. The following testing measures are employed to assay for the effectiveness of the vaccine; the embodiment below encompasses the candidate reservoir-targeted vaccine for Lyme disease. Testing involves assaying for bacterial strain identity and purity, plasmid sequence based upon restriction digestion and sequencing, and protein expression following the standard operating procedures for the sterility testing of modified live biological products in accord with 9 CFR 113.27(b). Vaccine efficacy validation and testing further follows that which is in accord with VSM 800.202.

EXAMPLE 1

Vaccine Biologic Purity and Identity

This study relates to methods for confirmation identity and purity of *E. coli* bacterial antigenic expression vehicle culture.

In this study, to assay for the viable/active culture required for the potency and efficacy of the vaccine, each of 10 bottles containing 40 mL Fluid Thioglycolate was inoculated with 0.2 mL from the $OD_{600}$=1.2 culture sample vial. The bottles were incubated for 14 days at 30-35° C. Additionally, each of 10 bottles containing 40 mL Trypticase Soy Broth was inoculated with 0.2 mL from the sample vial. The bottles were incubated for 14 days at 20-25° C. At the conclusion of the 14-day incubation period all 20 bottles displayed growth. No extraneous growth was observed in any of the bottles when examined macroscopically.

From each bottle, 0.2 mL of sample was plated onto Trypticase Soy Agar with 5% sheep blood and incubated for 24 hours at 37±2° C. After the 24-hour incubation, the colony morphology for each sample vial was uniform and consistent with that of *E. coli*. Microscopic examination revealed a uniform gram-negative rod consistent with that of *E. coli*.

The identity of the microorganism was confirmed as *E. coli* using a 96 well Biolog Microstation System, following the procedures for the Identification of Microorganisms. The Biolog Microstation System identified the organism as *E. coli* with an 80.4% likelihood score.

EXAMPLE 2

Vaccine Antigen Expression Stability

The following study relates further to the methods for confirming plasmid stability and isolation from culture, identified as *E. coli* per that which is outlined in Example 1.

For 2 different sample vials, A and B, a 10-fold dilution series was made using 1% bacto peptone. From the $10^{-7}$ dilution, 0.1 mL was transferred onto LB plates containing 50 μg/mL Kanamycin and incubated for 24 hours at 37±2° C. For both A and B sample plates, three culture tubes containing 10.0 mL of LB broth with 100 μg/mL Kanamycin were inoculated using isolated colonies and incubated for 16 hours with continuous, low level agitation at 37±2° C. The tubes were then centrifuged at 8000 rpm (×4300 g) for 3 minutes to pellet the cells. The Qiagen Spin MiniPrep Kit was used to isolate plasmid DNA from the cell cultures. The plasmid DNA yield was quantified using the NanoVue spectrophotometer. The samples with the highest plasmid yield, A1 and B 1, 53.5 μg/mL and 83.0 μg/mL respectively, were selected for additional analysis. The isolated plasmid was then used for both sequencing and restriction digest analysis to verify the OspA genes successful transformation into the *E. coli*.

Restriction Digest of Isolated Plasmid. The isolated OspA plasmid sample A1 and B1 were digested with BamHI and Ndel as presented in Table 1 (These samples were incubated at 37±2° C. for 1 hour).

TABLE 1

| Restriction Digest Dilution Scheme | |
|---|---|
| OspA Plasmid sample (A1 or B1) | 10 μL |
| NE Buffer 3.1 | 5 μL |

TABLE 1-continued

| Restriction Digest Dilution Scheme | |
|---|---|
| BamHI | 1 μL |
| NdeI | 1 μL |
| DI water | 33 μL |

An undigested isolated OspA plasmid sample of A1 and B1 were diluted as presented in Table 2.

TABLE 2

| Undigested OspA Dilution Scheme | |
|---|---|
| OspA Plasmid Sample (A1 or B1) | 10 μL |
| DI water | 40 μL |

One (1.0) μL of the 1 kb ladder was diluted with 9 μL of DI water. □Five (5.0) μL of the supercoiled DNA ladder was diluted with 5 μL of DI water. Ten (10.0) μL of each sample was added to 2 μL of 6' loading dye. Twelve (12) μL of each sample was loaded onto a 1% agarose gel+4 μL of Ethidium Bromide as presented in Table 3.

TABLE 3

SDS PAGE Lane Key

| Lane | Sample |
|---|---|
| 1 | 1 kb ladder |
| 2 | 2 SC ladder |
| 3 | 3 Undigested A1 |
| 4 | 4 Digested A1 |
| 5 | 5 Undigested B1 |
| 6 | 6 Digested B1 |

The gel was run at 100V for 90 minutes with 0.5× TBE+24 μL of Ethidium Bromide. The gel was analyzed on Transilluminator with UV light. Acceptance criteria requires that (1) the OspA band must align with the 1 kb ladder band at 1.0 kb. The Plasmid backbone must align with the ladders just above the 4 kb band; (2) the undigested samples must have a band slightly above the 5 kb band on the ladders; and (3) bands were present and at the appropriate size (See Table 4 and FIGS. 1 and 2). The result was satisfactory.

TABLE 4

Estimated Lengths of DNA Fragments after Digestion

| | Estimated Fragment Size |
|---|---|
| OspA | 1079 bp |
| Plasmid Backbone | 4301 bp |
| Uncut Plasmid | 5380 bp |

Sequencing T7 region of Plasmid. The primers used in the sequencing of the T7 region of the expression plasmid construct included (1) the T7 Promoter Primer of sequence: TAATACGACTCACTATAGGG (SEQ ID NO: 1), and (2) the T7 Terminator Primer of sequence: GCTAGTTAT-TGCTCAGCGG (SEQ ID NO: 2). Isolated plasmids and T7 Primers were sent to Iowa State to be sequenced in both the forward and reverse directions using the Sanger method. Results demonstrated that the forward and reverse orientation sequences had an identity score of 100% (FIG. 3) and 99% (FIG. 4) respectively.

EXAMPLE 3

Methods for Assaying Vaccine Protein Antigen Expression

The demonstration of plasmid stability and expression is validated via western blot analysis for assay of the expressed protein product, OspA. Protein extraction for western blot analysis followed with an expansion of the ospA-vectored E. coli cultures. E. coli samples were inoculated into 10 mL of LB+Broth containing 100 µg/mL Kanamycin and incubated overnight with continuous, low level agitation at 37±2° C. The sample was centrifuged at 8000 rpm (×4300 g) for 3 minutes to pelletize the cells. The supernatant was then discarded. The pellet was resuspended in 1 mL of ice-cold PBS. The sample was centrifuged at 8000 rpm for 3 minutes to pelletize the cells. The supernatant was then discarded. The pellet was resuspended in 1 mL of ice-cold PBS and transferred to a clean 1.5 mL microcentrifuge tube. The sample was centrifuged at 8000 rpm (×4300 g) for 3 minutes to pelletize the cells. The supernatant was then discarded. The pellet was resuspended in 1 mL of an ice cold 20 mM tris-HCl solution and allowed to stand on ice for 30 minutes as a cell lysis step. The resulting cell lysate was centrifuged at 10,000 rpm (×6720 g) for 10 minutes. The supernatant containing the soluble protein fraction was transferred into a clean microcentrifuge tube. The cell pellet containing the insoluble protein fraction was resuspended in 1 mL of an ice-cold 20 mM tris-HCl solution. Both soluble and insoluble protein fractions were used for western blot analysis.

Western blot. After protein was extracted, samples were prepared as presented in Table 5.

TABLE 5

| Protein Reducing Agent + Buffer Reaction | |
|---|---|
| OspA Sample A1, B1 or PC | 6.5 µL |
| Sample Buffer | 2.5 µL |
| DTT | 1.0 µL |

Samples were heated at 70° C. for 10 minutes on a heat block. Ten (10) µL of each sample was loaded onto a 4-12% Bis-Tris Gel as presented in Table 6.

TABLE 6

| Western blot Lane Key | |
|---|---|
| Lane | Sample |
| 1 | MWM |
| 2 | PC |
| 3 | Sample A1 |
| 4 | Sample B1 |

Figure 5:
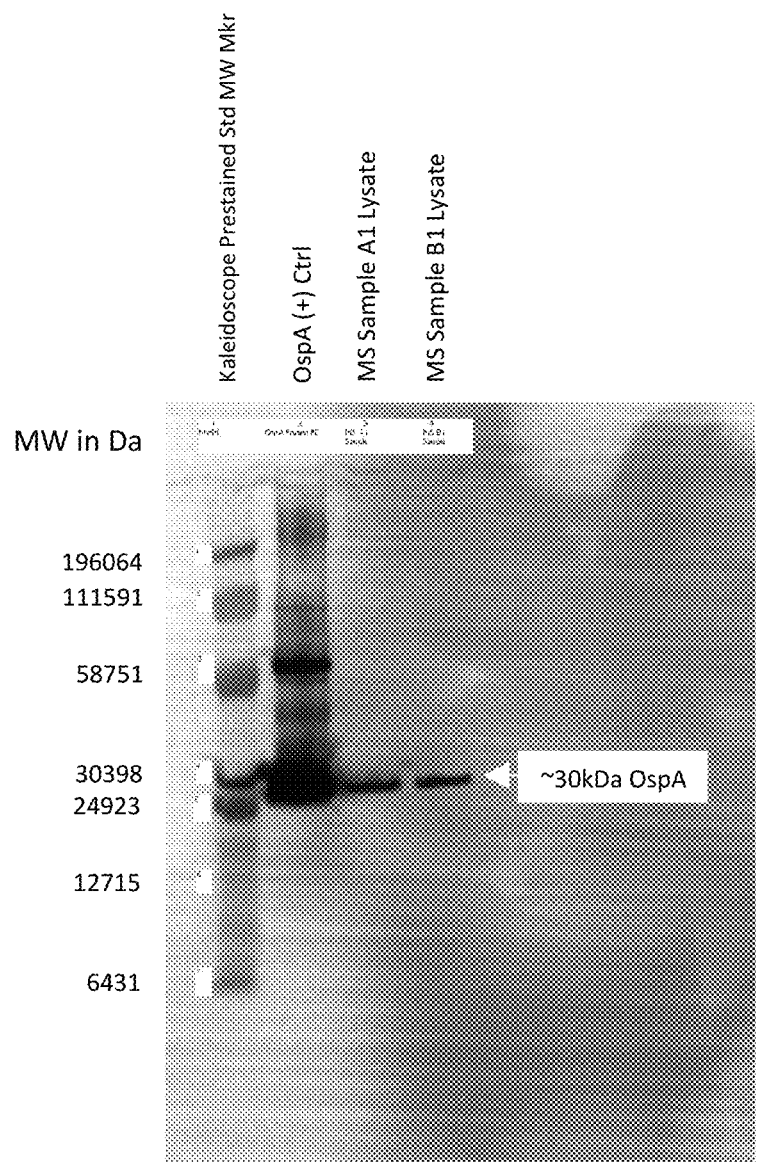
FIG. 5 is an image of the Western blotting analysis for OspA protein expression from ospA-vectored *E. coli*.
Figure 6:
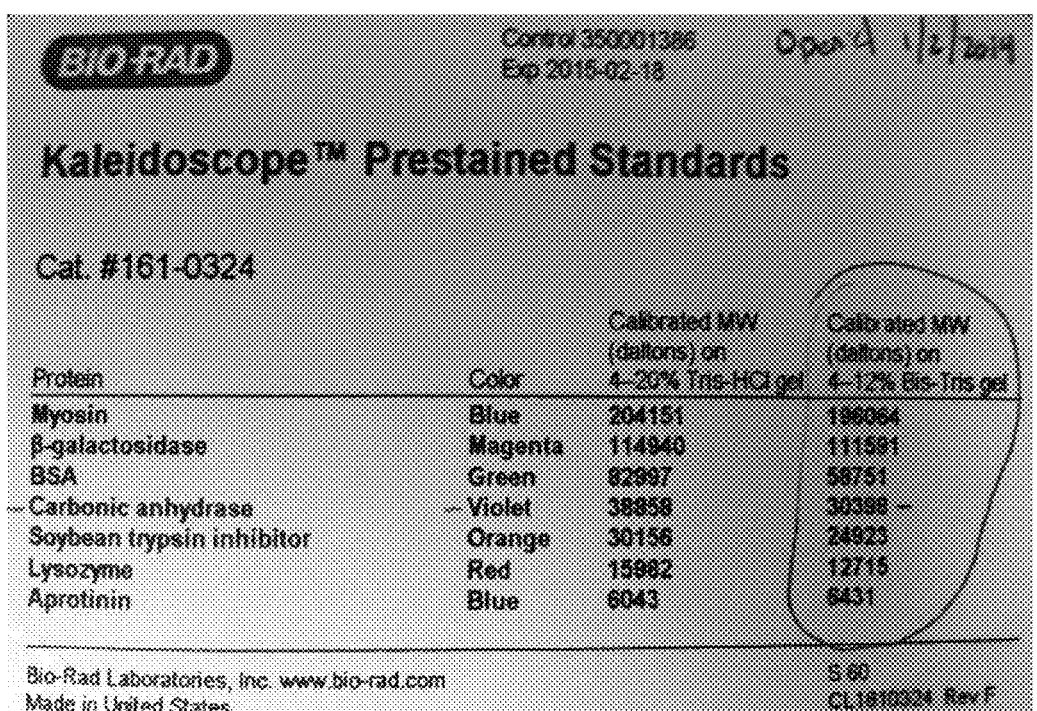
FIG. 6 is an image of protein molecular weight marker standards.

The gel was run at 220 v for 30 minutes on the Bio Rad gel system in 1× Novex MES SDS Running Buffer+1 mL Antioxidant. The PVDF transfer membrane, filter paper and pads were soaked in 1× NuPAGE Transfer Buffer (75 mL 20× NuPAGE Transfer Buffer+1.5 mL antioxidant+150 mL Methanol+1273.5 mL DI water). The gel was prepared with the transfer membrane and ran at 30V for approximately 1 hour. The OspA protein-transferred PVDF membrane was activated with Methanol for 2 minutes at room temperature. The membrane was dispensed into 1× TBST (100 mL TBS+900 mL DI water+500 µL Tween 20)+3% skim milk into reservoir and rocked the membrane for 1 hour. The solution was discarded and the OspA MAb LA2.2.1 hybridoma sup (100 µL OspA MAb+9.9 mL 1× TBST)+1% skim milk was then added and the membrane rocked for 1 hour at room temperature. The membrane was then washed with 1× TBST three times. The membrane was rocked for 5 minutes at each washing. The secondary antibody (goat anti-mouse IgG AP) (Dilution 1:1000) in 1× TBST+1% skim milk was added and rocked with the membrane for 30 minutes at room temperature. The membrane was again washed with 1× TBST three times. The membrane was rocked for 5 minutes at each washing. Five (5.0) mL of BCIP/NBT membrane phosphatase substrate was then added. This solution was allowed to develop the membrane and the reaction was stopped with the addition of water. The membrane was dried at room temperature. The acceptance criterion requires that a band must be present at the violet 30398 Daltons band on the MWM. Results demonstrated that a band was present at the 30398 Dalton for each sample (See FIGS. 5 and 6). The result was satisfactory.

E. coli testing positive for stable plasmid expression of OspA protein antigen, meets the criteria necessary for use as the biological whole cell vehicle of vaccine antigen and can be coated onto suitable substrate for administration to target animals.

EXAMPLE 4

Composition of Suitable Vaccine Carrier Substrate Material

In some embodiments, the substrates of the present disclosure are of a pelletized type, extruded, and/or of a non- or low-nutritional value. Further, said substrates may comprise ground corn, wheat middlings, cane molasses, calcium carbonate, animal fat, such as porcine fat preserved with butylated hydroxyanisole (BHA), dehulled soybean meal, ground oats, salt, dehydrated alfalfa meal, whole wheat, ground soybean hulls, fish meal, dried beet pulp, dicalcium phosphate, wheat germ, corn gluten meal, and soybean oil. In certain embodiments, the compositions of the present disclosure include extruded pellets; and in some embodiments, the extruded pellets are of high pellet durability index (PDI>90) and can be, for example, spheroid or cylindrical in shape. The high durability and spheroid shape of said pellet substrates allow pellets to maintain integrity and shape while being coated with vaccine in an efficient commercial drum tumbling coating process.

EXAMPLE 5

Composition of Vaccine Stabilization and Coating Matrix

In some embodiments, to accommodate vaccine for the coating process useful in the methods of the present disclosure, whole-cell bacterial biomass is first scaled up under standard fermentation methods to a cell density of entry into the stationary phase. Culture conditions supporting the growth of the whole-cell bacterial biomass follow those as presented by Studier (2005), for growth of cultures harboring the pET9c plasmid expression vector. Briefly, a single-colony isolate of the ospA-vectored BL21(DE3) *E. coli* is grown on Kan+ selection solid media. Isolates are individually grown overnight in 3 mLs of a TBY+Kan liquid selection media. The liquid culture is then passaged at a ratio of 1:1000 into TBY+Kan induction media to induce the expression of the T7 promoter driving expression of the ospA gene. In some embodiments, the biomass of the present disclosure undergoes hollow-fiber filtration for liquid media reduction to generate wet-cell paste (WCP). Reduction in liquid media involves washing the WCP to a suspension with PBS. To maintain a whole-cell antigen vehicle as the metric for dictating the minimal immunizing dosage (MID) the biomass is stabilized.

As used herein, PBS refers to phosphate-buffered saline, without the divalent cations of calcium and/or magnesium.

As used herein, the osmotic preconditioner solution useful in the methods of the present disclosure refers to a solution of a final concentration of 500 mM to 625 mM sucrose fully dissolved in PBS. The osmotic preconditioner solution serves as a (1) cryo-stabilization matrix for cryopreservation of the biological composition, and/or as a (2) matrix solution to osmotically stabilize the whole-cell bacterial cells under the down-stream encapsulation processing and drying conditions of anhydrobiosis. In some embodiments, the use of a final concentration of 100 mM trehalose is employed as the sugar used in the stabilization matrix.

In some embodiments, the osmotic preconditioning process ensues by slowly mixing the biomass-PBS suspension 1:1 with a 1 mM to 1.25 mM concentrated solution of stabilization matrix at 4° C., yielding a final concentration at 500 mM to 625 mM sucrose in PBS. This embodiment yields the osmotically stabilized liquid vaccine component. The liquid vaccine component can be used immediately as the composition applied to suitable substrate material, or frozen down to −80° C. under coating can be performed.

In some embodiments, sodium alginate is used as an encapsulation matrix platform for stabilizing viable cells under conditions of anhydrobiosis. In certain embodiments, the methods described in references such as the *Standard Guide for Immobilization or Encapsulation of Living Cells or Tissue in Alginate Gels* (ASTM, Designation F2315-10, 2010, reference provided by FMC Biopolymer) and that which is outlined according to Smidsrod and Skjak-Braek, *Trends. Biotechnol.*, 8:71, 1990, are followed for the preparation of the sodium alginate mixture.

An example is presented of the linear chemical equation representing the crosslinking reaction: 2Na-Alginate+$CaCl_2 \rightarrow$Ca-Alginate+2NaCl. In some embodiments, hydrocolloid polymers present as enteric polymers. In some embodiments, polymeric stabilization of some or all of the components of the compositions of the present disclosure may protect the components from the digestive pH of the stomach, thereby conserving the components for targeted release in the gut. For example, in certain embodiments, an orally administered biological vaccine composition comprises one or more ingredients/components that has been polymerically stabilized. In some embodiments, a composition of the present disclosure comprises sodium alginate that has been cross-linked with calcium.

In some embodiments, an aqueous suspension of sodium alginate, such as a 1 to 4% suspension, is prepared in a solution of 500 mM to 625 mM sucrose in distilled/deionized water. The suspension is mixed for about 6 hours by agitation at room temperature, or until fully dissolved yielding a suspension of a sodium alginate-sucrose syrup. The osmotically stabilized liquid vaccine component is then gently mixed with the sodium alginate encapsulation matrix solution at room temperature. The liquid vaccine—sodium alginate mixture is then applied onto spheroid animal food pellets. The semi-dry vaccine—sodium alginate coating is then subsequently coated with a sprayed mixture of 100 mM to 225 mM calcium lactate (up to 7% solution, as a source for crosslinking multivalent ion with enhanced taste; a 5% to 7% solution of calcium chloride may also be used) as a cross-linking agent to facilitate the generation of a calcium-alginate micro-encapsulated bacterial cell layer upon the pellet substrates, as illustrated in the schematic in FIG. 7. Calcium-alginate cross-linked/encapsulation maintains the viability and immunogenic integrity of the bacterial-based vaccine antigen.

EXAMPLE 6

Methodology for Spray Coating Stabilized Vaccine as a Top-Dressing Onto Substrate Composition Spray drying is a common practice for the stable drying, for enhanced shelf life, of biological materials. The prior art includes the application of technologies for the spray drying of biological materials for collection and utilization downstream. Biological stability is enhanced through the process of encapsulation whereby said biological material is in composition with a hydrocolloid polymer and then mixed with a cross-linking compound. Spray-dried encapsulated biological material is then collected for utilization. The present invention introduces the application of spraying a biological material, in composition with a hydrocolloid or other encapsulation composition, onto a substrate material. The substrate material serves as a solid-support carrier onto which the spray-coated biological material may be subsequently sprayed with (1) cross-linking agents to facilitate encapsulation, and (2) moisture barrier glazes or shellacs, flavoring or scented baiting attractants. The coated pellets can then be subjected to a gentle drying process whereby the coated materials may be dried.

Substrate materials of spheroid, or "cleaned" pellet substrates facilitate a "fluid" tumbling process during a coating-drum tumbling process. Pellet substrates are fed into a coating drum at a given rate to effectively yield appropriate dose coverage when spray-coated. Pellets are gently and uniformly rolled/tumbled within the drum while concurrently being spray-coated with the sucrose-stabilized/alginate-encapsulated bacteria. Spraying is tightly controlled (can be electrostatically delivered) and automatically linked to the tumbling duration to ensure even coating coverage, and proper dosage equating to the designated MID as measured in colony forming units (CFU) per pellet. The secondary spray coating facilitates the crosslinking reaction as reacted by calcium. An optional tertiary coating of a final outer sealant of a confectionary glaze and/or pharmaceutical shellac in combination with an attractant/flavor additive facilitates free-flowing pellets for handling, storage, and distribution; flavor additive provides palatable attractant to target animal reservoir hosts of Lyme disease. Drying occurs while tumbling, or by spreading product across a high surface-area drying table. Process yields high throughput under continuous batch operation.

Figure 8:
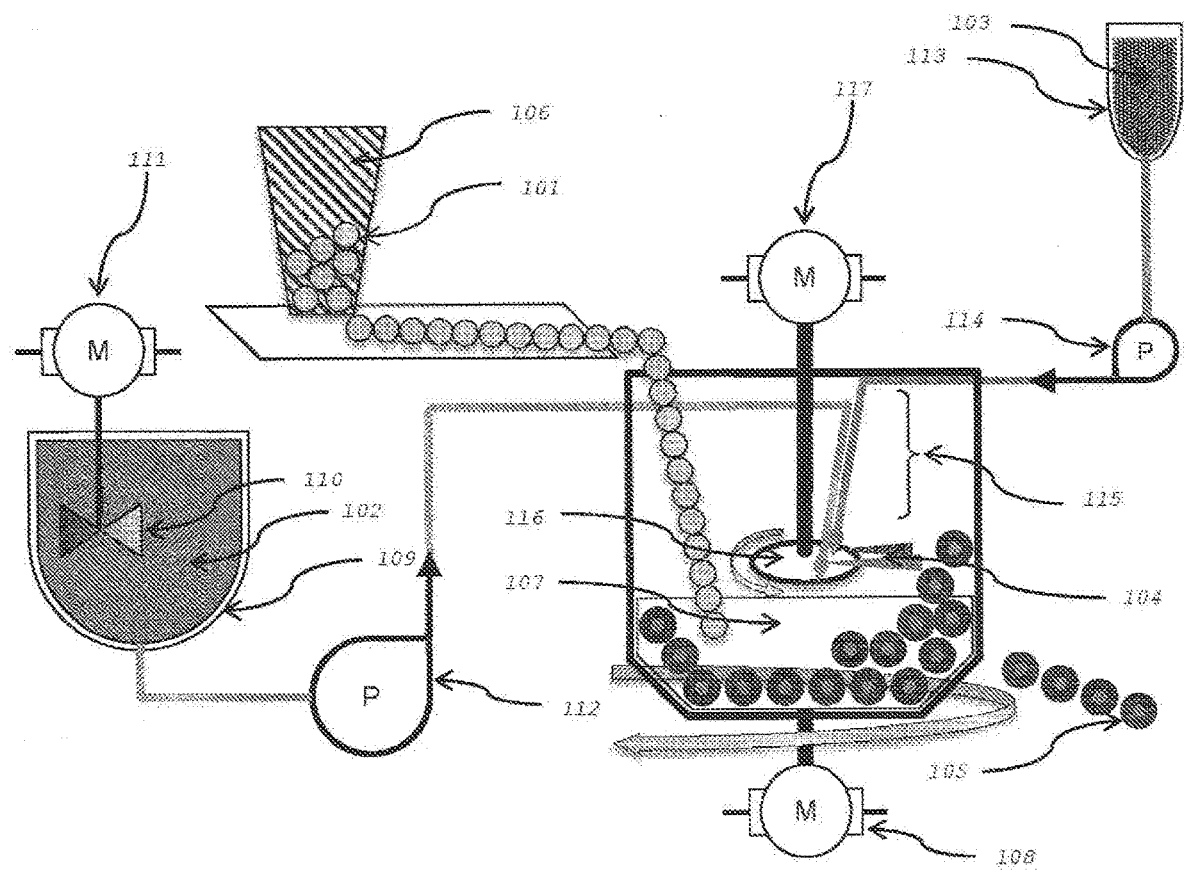
FIG. 8 is a diagram showing a current operational example for employment of drum-coating processing and formulation.

In some embodiments, the employment of a method for centrifugally applying the biological material in composition with a hydrocolloid or other encapsulation matrix composition, and subsequent cross-linking agent yielding a coating on the surface of the pellets is considered using centrifugal batch coating technology. As illustrated in FIG. 8 and used herein in the present invention disclosure, the use of centrifugal coating equipment is employed for the high throughput commercial operation of efficiently coating the substrate pellet (herein, "pellets") material. The pellets (101) are held in bulk (batch hopper, 106) for entry into the coating drum (107) where they are gently folded and agitated under constant revolution, as driven by a standard motorized system (108). Biological material in composition with the sodium alginate hydrocolloid stabilization matrix (Reagent A, 102) (or other encapsulation composition) is maintained in reserve (109) and in suspension via an onboard motor-driven mixer (110-111). Similarly, calcium lactate crosslinking agents (Reagent B, 103) and moisture barriers are also held in reserve (113). Both reagents are added in succession (115) via a peristaltic pumping process (112, 114) and coated onto the folding pellets through an atomization process (104) facilitated via dispensing onto a separate motorized (117) spinning centrifugal disc (116) positioned central to the revolutions of the folding substrate, thereby evenly coating the pellets (105) with the designated MID.

EXAMPLE 7

Methods for Demonstrating Vaccine Stability

Figure 9:
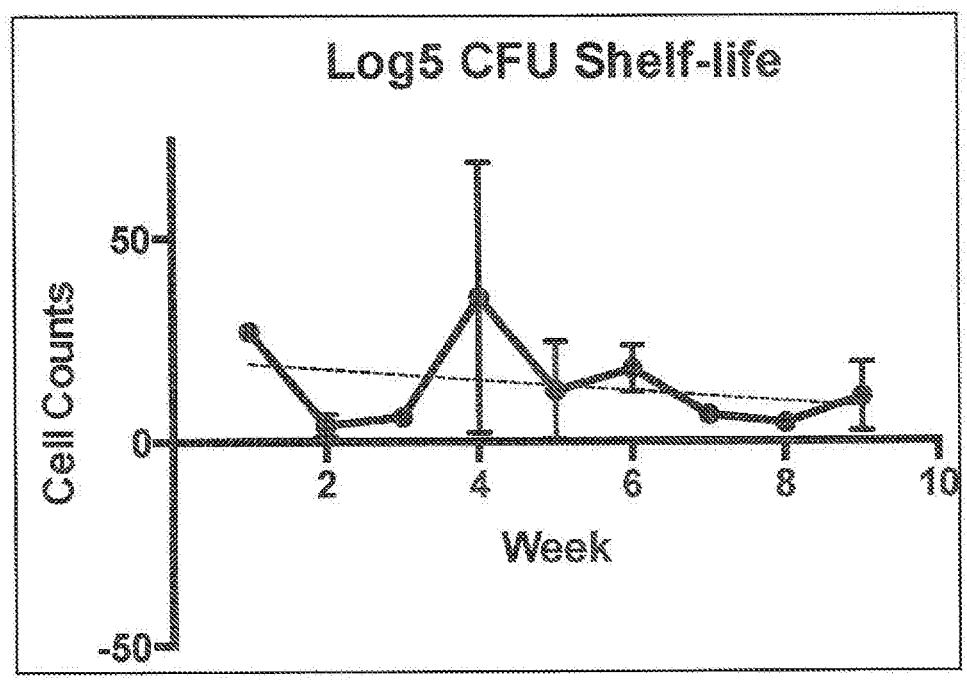
FIG. 9 is a presentation of the shelf life of the vaccine embodiment disclosed herein as assayed by CFU counts generated from vaccine, as a function of storage time.

An effective shelf life of the embodiment presented herein is essential to accommodate distribution schedules and campaigns. Stabilized vaccine-coated pellets present as water-insoluble articles for oral administration, enterically stable for effectively administering the vaccine to the GALT. Stability/shelf-life analyses were conducted on dried, vaccine coated pellets. Briefly, each individual vaccine pellet test article was rehydrated in a 4 mL volume of 55 mM sodium citrate solution of HEPES buffered saline, at a pH of 7.4. Volumes were incubated at 35° C. for 1 hour under agitation. 100 µL of the pellet supernatant, containing released/de-encapsulated viable OspA-vectored whole cell *E. coli* was plated out on a TB+Kan agar plate and cultured overnight for the assessment of colony growth. Resulting colonies were calculated as approximate CFU per mL representative of the colonies release upon rehydration from each vaccine-coated pellet; the resultant CFU counts were evaluated as a surrogate marker of the vaccine stability and decay (shelf life) over time. This procedure was employed weekly upon post-production vaccine-coated pellets for up to 10 weeks. Results as presented in FIG. 9 suggest that the viability of the active vaccine component, the *E. coli* antigenic vehicle, maintain stable and viable, with a decay factor of 2 over an 8-week assay period.

EXAMPLE 8

Methods for Demonstrating Vaccine Efficacy

Vaccine efficacy is determined based upon ability to induce sero-responsiveness in an animal following administration of antigen. The employment of an indirect enzyme-linked immunoabsorbant assay (ELISA) for antibody titers raised against an antigen or immunogen is a surrogate marker for the vaccine efficacy. As used herein, the use of the indirect ELISA methodology is qualified for the detection of serum antibodies directed against OspA. The assay is conducted wherein a purified OspA target/capture antigen protein is coated onto a solid support. Primary antibodies in the form of an OspA-specific monoclonal antibody (positive control, MAb LA2.2), or OspA serum antibodies (test subject) are then allowed to bind to the target antigen. A secondary antibody conjugate specific to the primary antibody is then added, and the reaction is developed to indicate the relative levels of serum OspA-specific responsive antibodies. The procedurals follow with the use of flat-bottom wells. The purified protein is then diluted to a final concentration 0.5 to 2 µg/mL in coating buffer (10 mL of coating buffer solution for one plate—96 wells), and to each well is dispensed at a volume of 100 µL (using an 8-channel pipette). The plate is covered and incubated at room temperature, with no shaking, for 1 h or at 4 C overnight (ideally). The solution is discarded and dried out on a paper towel. 300 µL of blocking buffer is added (PBST+1% BSA) to each well. The plate is again covered and incubated at 37° C. (no shake) for 1 h. The plate is washed 3× for each well with 300 .mu.L 1× PBST. To each well is added 100 .mu.L of diluted serum sample (1:100, 1:500) in blocking/sample diluent; for control wells, a MAb standard curve (500, 250, 125, 62.5, 31.25 ng/mL) is added. The plate is covered and incubated at room temperature for 1 h. The solution is discarded and again dried out on a paper towel. Each well of the plate is washed 4× with 300 µL 1× PBST (for ELISA). Dilute Bt-MAb purified protein at a final concentration 0.3 µg/mL in blocking/sample diluent (make 10 mL of coating buffer solution for one plate—96 wells) is dispensed at 100 µL in each well (using an 8-channel pipette). The plate is covered and incubated at room temperature for 1 h, after which the solution is discarded and the plate dried on a paper towel. Each well is washed 4× with 300 µL 1× PBST (for ELISA). Neutravidin conjugated HRP is diluted 1:1000 in blocking/sample diluent and added to each well at a volume of 100 µL. The plate is covered and incubated at room temperature for 30 min, after which the solution is discarded and the plate dried out on a paper towel. The plate is washed 4× in each well with 300 µL 1×PBST (for ELISA). 100 µl of SureBlue (KPL) substrate is added to each well (the positive samples will turn blue). The plate is covered and incubated at room temperature between 30 min and 1 h. The absorbance is read at 650 nm for blue color and 450 nm for yellow color after addition of 100 µL of stop solution (KPL).

Figure 10:
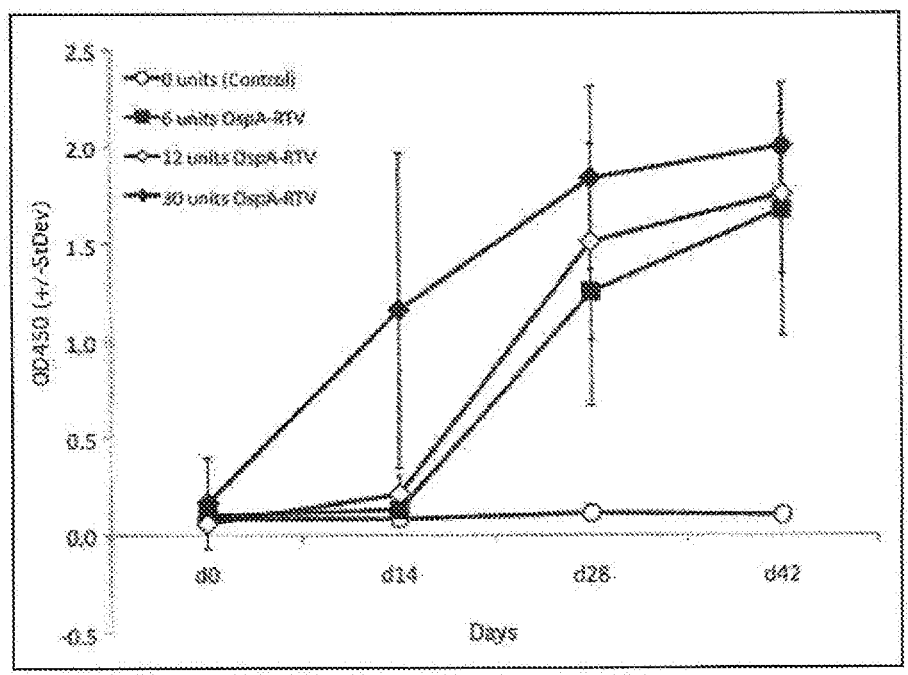
FIG. 10 represents anti-OspA antibody titer load in response to vaccine administration employing ospA-vectored *E. coli*.

As disclosed herein, the vaccine efficacy, or sero-protection is considered by assessing OspA-specific serum antibody titers equivalent to an $OD_{450}$ value as assayed by ELISA. Early optimization studies conducted on the core vaccine technology formulated as presented in Richer et al., *Clin. Vaccine Immunol.* 18:1809, 2011, and also disclosed herein (as referenced in U.S. Pat. No. 8,821,893, incorporated by reference in its entirety) sought to define the sero-responsiveness in mice in response to oral vaccine administration as measured by the qualified ELISA methods. A vaccine "unit" represents a dose and equates to approximately log $5 \times 10^5$ CFU. Multiple dosages equating to 0, 6, 12, and 30 units were administered weekly (days 0, 14, 28, and 42) to mice for up to 6 weeks. As presented in FIG. 10, the sero-response peaks around an $OD_{450}$ serum antibody titer equivalent of approximately 1.5. For commercial application, it is considered relevant that a minimum number of dosages be applied in order to generate the most efficacious sero-response, thereby defining the MID. From the results presented in FIG. 10, a weekly dosage of up to 6 dosages total was considered for the commercial evolution of the vaccine technology application disclosed in the present subject matter; the data demonstrate that an $OD_{450}$ serum antibody titer equivalent to approximately 0.6 is obtained after about 21 days of vaccine administration at a dosage of 6 units/week.

Experimental evidence has further demonstrated efficacy of the core vaccine technology when administered orally across multiple mouse species. Study summaries are outlined in Table 7.

TABLE 7

Summary of Vaccine Efficacy Study

| Study # | 1 | 2 | 3 | 4 |
|---|---|---|---|---|
| # Mice | 4 | 68 | 6 | 6 |
| Bait Form | RTV | RTV | USB Vaccine | USB Control |
| Dosing | Weekly | Daily | Weekly | Weekly |
| Dosage | 1 dose/week | Ad Libitum | 1 dose/week | 1 dose/week |
| Duration | 4 weeks | 1 Year | 3 weeks | 3 weeks |
| Assayed | Weekly | Weekly | Week 4 | Week 4 |
| Challenge | Yes, experimental | Yes, wild-type | N/A | N/A |
| Response | Neutralizing | Neutralizing | Efficacy | N/A |

Study 1 is a laboratory-based Borrelia challenge study, conducted as presented in Richer et al., Clin. Vaccine Immunol. 18:1809, 2011, and also disclosed herein, as referenced in U.S. Pat. No. 8,821,893 B2. A total of 4 outbred white-footed mice (Peromyscus leucopus) were evaluated as the subject animals in the study, as representative wild, reservoir-targeted animals for vaccine administration. Vaccine (reservoir-targeted vaccine, RTV) was generated, as described in Richer et al., 2011. Vaccine was administered weekly at a dosage of one dose per week, for a total of 4 weeks. A Borrelia challenge was performed 2 weeks after the last dose, as presented in Richer et al., 2011, to assess the efficacy of the vaccine to neutralize Borrelia infection. Briefly, 6 to 8 B. burgdorferi-infected nymphal ticks were placed on the back of the head of subject animals and allowed to remain for 3 days until falling off naturally upon engorgement with the blood meal. Mouse tissues (heart and bladder) and serum were then harvested. Tissues were assayed for Borrelia infection by culturing in BSK-H medium for up to 6 weeks at 34° C., with cultures being checked weekly by dark-field microscopy. Lack of Borrelia culture (0 viable spirochetes cultured from isolated mouse tissue) was indicative of infection neutralization by the vaccine administration and resultant anti-OspA titer loads. Neutralizing OspA-specific systemic IgG responsive titers were measured in harvested serum samples by ELISA. For commercial application, this study defined the MID needed to induce a protective immune response (FIG. 11, Study 1).

Study 2 is a translation of Study 1 to an R&D-based prospective 5-year field trial. The core vaccine technology (RTV) was developed as presented in Richer et al., J. Infect. Dis. 209:1972, 2014. As part of the study data presented in FIG. 11, Study 2 are representative of results from a vaccination campaign where vaccine was administered daily and animals were monitor and assayed weekly for sero-responsiveness to the OspA antigen. Results from 68 evaluated mice demonstrated that oral vaccination of P. leucopus using the lab-optimized MID of the vaccine core technology led to serum antibody titers as measured by ELISA effective at neutralizing the tick nymphal infection prevalence of Borrelia (natural challenge model). From this study a resulting mean $OD_{450}$ OspA-specific serum antibody titer equivalent to 0.6 was indicative of the sufficient correlate of protection required by the MID administered. The study further concluded that the administration of the vaccine in the field over the course of a 5-year campaign led to a reduction of up to 76% in the nymphal infection prevalence.

Study 3 is a laboratory-based study, conducted on the commercial vaccine, the formulation of which is the presently disclosed subject matter (USB Vaccine). The C3H inbred strain of mice was employed. Mouse bait pellets were used as the substrate onto which was coated stabilized vaccine at an MID of $5 \times 10^5$ CFU. Mice each received one dose per week over a total of three weeks of dosing; the mice were assayed by ELISA for sero-responsiveness at the end of the 4$^{th}$ week of the study. Results were compared to non-vaccinated controls (USB Control, Study 4). Results obtained from vaccinated animals demonstrated a sero-response, after only 3 dosages, in all 6 mice assayed in comparison to those animals administered non-vaccine-coated pellets (FIG. 11, Study 3 and 4).

Figure 11:
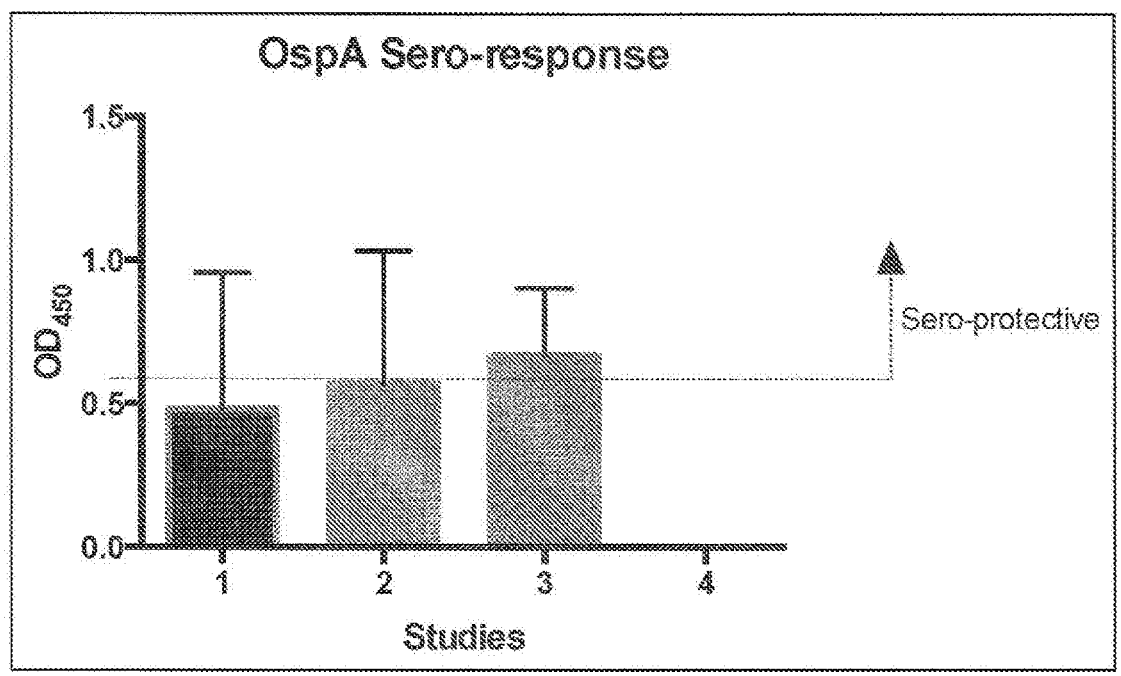
FIG. 11 represents the efficacy of the embodiment disclosed herein as aligned with the studies establishing vaccine efficacy. Data establish the threshold levels of seroprotective OspA antibody titers equating to vaccine efficacy.

FIG. 11 further presents a comprehensive summary of the minimum $OD_{450}$ OspA serum antibody titer equivalents required to establish correlates of protection against Borrelia. Efficacy values have been defined by mouse serological OspA-specific antibody titers equivalent to an absorbance of $OD_{450} \geq 0.6$. When all laboratory and field data are normalized to the $OD_{450}$ equivalents of sero-responsiveness, the data all present in collective alignment.

As disclosed herein, the vaccine efficacy, or sero-protection is further considered by assessing the OspA-specific neutralizing antibody potential of the serum antibody titers against a Borrelia culture via borreliacidal assay. The borreliacidal assay was based on a previously described method (Earnhart et al., Vaccine. 25:466, 2007).

All immunized sera samples were field-harvested from vaccine-immunized and control animals and were immediately placed on ice until aliquoted in the laboratory. Immunized sera samples were rank-ordered per $OD_{450}$ OspA titer equivalents, yielding 16 8-fraction pooled samples totaling 48 µL per sample, as a representative blend of the acquired sample spread.

The assay commenced on day 0 with Borrelia inoculation (16 µL of a $1 \times 10^4$ cell/mL culture, ATCC #35210) of the vaccine-immunized serological samples (8 µL each). Borrelia culture growth was sampled on Days 1 and 7 post-inoculation from which DNA was extracted and Borrelia outgrowth was assayed via copy number measurement of the spirochete flagellin gene (flaB) by qPCR, as a quantitative surrogate marker of growth.

The flaB primers used in the qPCR reaction included (1) the flaB F:

```
                              (SEQ ID NO: 4)
TCTTTTCTCTGGTGAGGGAGCT,
and (2) the flaB R:
                              (SEQ ID NO: 5)
TCCTTCCTGTTGAACACCCTCT.
```

Figure 12:
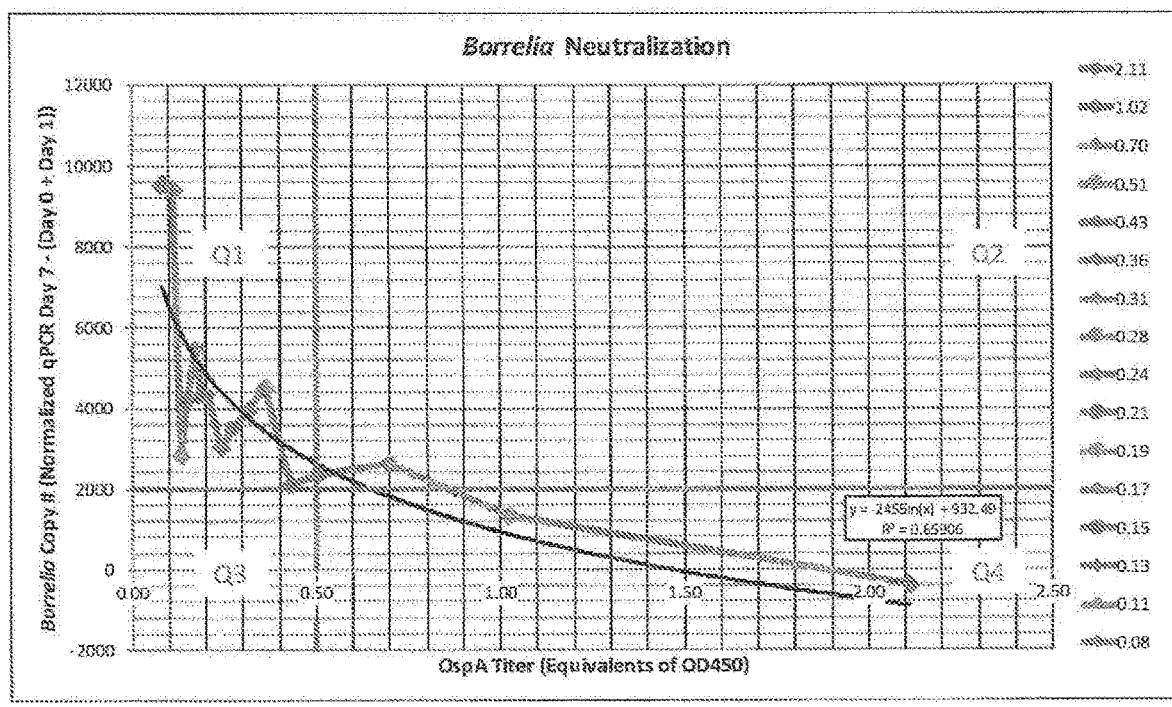
FIG. 12 presents a neutralization assay for in vitro growth inhibition of *Borrelia burgdorferi* as a direct measure of OspA-specific anti-sera function was employed as a function-oriented immunoassay to assess OspA-specific seroprotective immunoresponse against the spirochete *Borrelia burgdorferi*.

Results presented in FIG. 12 demonstrate Borrelia neutralization (borreliacidal activity) dependent upon an OspA titer as a serological correlate of protection index. To establish the correlate of protection threshold, an OspA-responsive serological-dependent reduction in Borrelia culture by 80% is considered. From a maximum approximate copy number of 10,000, an 80% growth reduction yields a Borrelia copy number of approximately 2000, correlating to an $OD_{450}$ OspA titer equivalent of 0.428 (defined by Quad 1 in FIG. 12 below). Conservatively, an $OD_{450}$ OspA titer equivalent equal to or greater than 0.5 is therefore proposed as the serological correlate of protection, an index above which OspA neutralizing titers are borreliacidal and below which OspA titers may not fully yield borreliacidal properties.

INCORPORATION BY REFERENCE

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

REFERENCES

Bowman and Clements, "Differential Biological and Adjuvant Activities of Cholera Toxin and Escherichia coli Heat-Labile Enterotoxin Hybrids", *Infect. Immun.* 69(3): 1528-1535, 2001.

Chen and Cerutti, "Vaccination Strategies to Promote Mucosal Antibody Responses", *Immunity.* 33: 479-491, 2010.

Earnhart et al. "Development of an OspC-based tetravalent, recombinant, chimeric vaccinogen that elicits bactericidal antibody against diverse Lyme disease spirochete strains", *Vaccine.* 25:466-80, 2007.

Erdile et al., "Role of Attached Lipid in Immunogenicity of *Borrelia burgdorferi* OspA", *Infect. Immun.* 61(1): 81-90, 1993.

Flanagan et al., "Oral Administration of Escherichia coli in Enteric Coated Microparticles Induces Serum Antibodies Against Lipopolysaccharide Antigens", *J. Endotoxin Res.* 3(6): 481-489, 1996.

Fujkuyama et al., "Novel Vaccine Development Strategies for Inducing Mucosal Immunity", *Expert Rev. Vaccines.* 11(3): 367-379, 2012.

Mazzitelli et al., "Production and Characterization of Alginate Microcapsules Produced by a Vibrational Encapsulation Device", *J. Biomat. Appl.* 23: 123-145, 2008.

Neutra and Kozlowski, "Mucosal Vaccines: the Promise and the Challenge", *Nature Rev. Immunol.* 6: 148-158, 2006.

Ogra et al., "Vaccination Strategies for Mucosal Immune Responses", *Clin. Microbiol. Rev.* 14(2): 430-445, 2001.

Richer et al., "Reservoir Targeted Vaccine for Lyme Borreliosis Induces a Yearlong, Neutralizing Antibody Response to OspA in White-Footed Mice", *Clin. Vaccine Immunol.* 18(11): 1809-1816, 2011.

Richer et al., "Reservoir Targeted Vaccine Against Borrelia burgdorferi: A New Strategy to Prevent Lyme Disease Transmission", *J. Infect. Dis.* 209(12): 1972-1980, 2014.

Smidsrod and Skjak-Braek, "Alginate as Immobilization Matrix for Cells", *Trends Biotechnol.* 8(3): 71-78, 1990.

Woodrow et al., "Mucosal Vaccine Design and Delivery", *Annu. Rev. Biomed. Eng.* 14: 17-46, 2012.

---

SEQUENCE LISTING

SEQ ID NO: 1: T7 Promoter Primer of sequence
TAATACGACTCACTATAGGG

SEQ ID NO: 2: T7 Terminator Primer of sequence
GCTAGTTATTGCTCAGCGG

SEQ ID NO: 3
>gi|365823346: 9457-10278 Borrelia burgdorferi
B31 plasmid lp54, complete sequence
ATGAAAAAATATTTATTGGGAATAGGTCTAATATTAGCCTTAATA
GCATGTAAGCAAATGTTAGCAGCCTTGACGAGAAAAACAGCGTTTCAGT
AGATTTGCCTGGTGAAATGAAAGTTCTTGTAAGCAAAGAAAAAAACAAAG
ACGGCAAGTACGATCTAATTGCAACAGTAGACAAGCTTGAGCTTAAAGGA
ACTTCTGATAAAAACAATGGATCTGGAGTACTTGAAGGCGTAAAAGCTGA
CAAAAGTAAAGTAAAATTAACAATTTCTGACGATCTAGGTCAAACCACAC
TTGAAGTTTTCAAAGAAGATGGCAAAACACTAGTATCAAAAAAAGTAACT
TCCAAAGACAAGTCATCAACAGAAGAAAAATTCAATGAAAAAGGTGAAG
TATCTGAAAAAATAATAACAAGAGCAGACGGAACCAGACTTGAATACAC
AGGAATTAAAAGCGATGGATCTGGAAAAGCTAAAGAGGTTTTAAAAGGCT
ATTTCTTGAAGGAACTCTAACTGCTGAAAAAACAACATTGGTGGTTAAAG
AAGGAACTGTTACTTTAAGCAAAAATATTTCAAAATCTGGGGAAGTTTCA
GTTGAACTTAATGACACTGACAGTAGTGCTGCTACTAAAAAAACTGCAGC
TTGGAATTCAGGCACTTCAACTTTAACAATTACTGTAAACAGTAAAAAAA
CTAAAGACCTTGTGTTTACAAAAGAAAACACAATTACAGTACAACAATAC
GACTCAAATGGCACCAAATTAGAGGGGTCAGCAGTTGAAATTACAAAACT
T GATGAAATTAAAAACGCTTTAAAATAA SEQ ID NO: 4: flaB Forward Primer sequence
TCTTTTCTCTGGTGAGGGAGCT SEQ ID NO: 5: flaB Reverse Primer sequence
TCCTTCCTGTTGAACACCCTCT

---

What is claimed is:

1. A method of controlling Lyme disease by vaccinating a subject in need thereof comprising orally administering to the subject a composition for oral delivery of a bait foodstuff, said bait foodstuff comprising: i) a bait substrate having a surface; ii) an effective amount of at least one antigenic agent layered over said substrate, wherein said at least one antigenic agent is stabilized within a stabilizer under conditions facilitating anhydrobiosis, said stabilizer selected from at least one of the group consisting of a hydrocolloid polymer and a plasticizing sugar, complexed in solution with a phosphate-buffered saline liquid carrier; and iii) a calcium salt cross-linking agent to facilitate encapsulation of said antigenic agent within said stabilizer on said surface of said substrate; wherein said antigenic agent is a bacterial vehicle, said bacterial vehicle defined by a recombinant whole-cell OspA-vectored *Escherichia coli* bacteria engineered to express at least one *Borrelia burgdorferi* antigen.

2. The method of claim 1 wherein said calcium salt cross-linking agent is selected from the group consisting of calcium lactate, calcium chloride, calcium sulfate, calcium carbonate, calcium acetate, calcium ascorbate, and any combination thereof.

3. The method of claim 1 wherein said stabilizer is both a hydrocolloid polymer and a plasticizing sugar.

4. The method of claim 3 wherein said hydrocolloid polymer is a sodium alginate.

5. The method of claim 1 wherein said effective amount of said antigen layer is an immunogenically effective amount with the minimal immunizing dosage (MID) of about $5 \times 10^3$ CFU to about $5 \times 10^7$ CFU.

6. The method of claim 1 wherein said bacterial vehicle is present in an effective amount of at least one antigenic agent coated or layered on said bait substrate, and wherein said recombinant whole cell bacteria is a plurality of killed whole-cell bacterial units expressing said at least one *Borrelia burgdorferi* antigen as a bacterin.

7. The method of claim 1 wherein the subject is a reservoir host of the Lyme disease cycle.

8. The method of claim 1 wherein the subject comprises a susceptible host of Lyme disease being a xenodiagnostic carrier selected from the group comprising an arthropod, an insect, a mammal, a bird, and a fish.

9. The method of claim 8 wherein said host is a mammal.

10. The method of claim 9 wherein said mammal is a feral animal comprising one or more of a mouse, a chipmunk, a squirrel, a shrew, a vole, a rat, a raccoon, an opossum, a skunk, a rabbit, and a deer.

11. The method of claim 8 wherein said mammal is a domesticated or companion animal comprising one or more of a dog, a cat, a cow, and a horse.

12. The method of claim 1 wherein the animal bait substrate is in an amount of about 85% to about 99% w/w of the bait foodstuff.

13. The method of claim 1 wherein the composition is a microencapsulated bead.

\* \* \* \* \*

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: T7 Promoter Primer of sequence

<400> SEQUENCE: 1
taatacgact cactataggg                                         20

<210> SEQ ID NO 2
<211> LENGTH: 19
<212> TYPE: DNA
<213> ORGANISM: Artificial Sequence
<220> FEATURE:
<223> OTHER INFORMATION: T7 Terminator Primer of sequence

<400> SEQUENCE: 2
gctagttatt gctcagcgg                                          19

```
<210> SEQ ID NO 3
<211> LENGTH: 822
<212> TYPE: DNA
<213> ORGANISM: Artificial Sequence
<220> FEATURE:
<223> OTHER INFORMATION: Borrelia burgdorferi B31 plasmid lp54

<400> SEQUENCE: 3
atgaaaaaat atttattggg aataggtcta atattagcct taatagcatg taagcaaaat      60
gttagcagcc ttgacgagaa aaacagcgtt tcagtagatt tgcctggtga aatgaaagtt     120
cttgtaagca agaaaaaaa caaagacggc aagtacgatc taattgcaac agtagacaag     180
cttgagctta aggaacttc tgataaaaac aatggatctg gagtacttga aggcgtaaaa      240
gctgacaaaa gtaaagtaaa attaacaatt tctgacgatc taggtcaaac cacacttgaa     300
gttttcaaag aagatggcaa aacactagta tcaaaaaaag taacttccaa agacaagtca     360
tcaacagaag aaaaattcaa tgaaaaaggt gaagtatctg aaaaaataat aacaagagca     420
gacggaacca gacttgaata cacaggaatt aaaagcgatg gatctggaaa agctaaagag     480
gttttaaaag gctatgttct tgaaggaact ctaactgctg aaaaaacaac attggtggtt     540
aaagaaggaa ctgttacttt aagcaaaaat atttcaaaat ctggggaagt ttcagttgaa     600
cttaatgaca ctgacagtag tgctgctact aaaaaaactg cagcttggaa ttcaggcact     660
tcaactttaa caattactgt aaacagtaaa aaaactaaag accttgtgtt tacaaaagaa     720
aacacaatta cagtacaaca atacgactca aatggcacca aattagaggg gtcagcagtt     780
gaaattacaa aacttgatga aattaaaaac gctttaaaat aa                       822

<210> SEQ ID NO 4
<211> LENGTH: 22
<212> TYPE: DNA
<213> ORGANISM: Artificial Sequence
<220> FEATURE:
<223> OTHER INFORMATION: flaB Forward Primer sequence

<400> SEQUENCE: 4
tcttttctct ggtgagggag ct                                               22

<210> SEQ ID NO 5
<211> LENGTH: 22
<212> TYPE: DNA
<213> ORGANISM: Artificial Sequence
<220> FEATURE:
<223> OTHER INFORMATION: flaB Reverse Primer sequence

<400> SEQUENCE: 5
tccttcctgt tgaacaccct ct                                               22
```